US007651846B2

(12) United States Patent
Morris

(10) Patent No.: US 7,651,846 B2
(45) Date of Patent: Jan. 26, 2010

(54) TREATMENT AND DIAGNOSIS OF CONDITIONS ASSOCIATED WITH ELEVATED ARGINASE ACTIVITY

(75) Inventor: Claudia R. Morris, Lafayette, CA (US)

(73) Assignee: Children's Hospital & Research Center at Oakland, Oakland, CA (US)

(*) Notice: Subject to any disclaimer, the term of this patent is extended or adjusted under 35 U.S.C. 154(b) by 0 days.

(21) Appl. No.: 11/002,956

(22) Filed: Dec. 1, 2004

(65) Prior Publication Data
US 2005/0158401 A1 Jul. 21, 2005

Related U.S. Application Data

(63) Continuation-in-part of application No. PCT/US2004/004369, filed on Feb. 13, 2004.

(60) Provisional application No. 60/447,373, filed on Feb. 14, 2003.

(51) Int. Cl.
C12Q 1/34 (2006.01)
G01N 33/50 (2006.01)
G01N 33/00 (2006.01)

(52) U.S. Cl. .............................. 435/18; 436/68; 436/86; 436/89; 436/116

(58) Field of Classification Search ........................ None
See application file for complete search history.

(56) References Cited

U.S. PATENT DOCUMENTS

| 4,096,037 | A | * | 6/1978 | Mia ............................. 435/18 |
| 4,507,314 | A | | 3/1985 | Niebes et al. |
| 5,217,997 | A | | 6/1993 | Levere et al. |
| 6,027,713 | A | | 2/2000 | Russell |
| 6,127,421 | A | | 10/2000 | Wideman, Jr. et al. |
| 6,165,975 | A | | 12/2000 | Adams et al. |
| 6,359,007 | B1 | | 3/2002 | Pearson et al. |
| 6,387,890 | B1 | | 5/2002 | Christianson et al. |
| 6,436,997 | B1 | | 8/2002 | de Tejada |
| 6,646,006 | B2 | | 11/2003 | Cooke et al. |
| 6,720,188 | B2 | | 4/2004 | Kaddurah-Daouk et al. |
| 6,956,131 | B2 | * | 10/2005 | Pitzele et al. ............... 562/560 |
| 2003/0003162 | A1 | | 1/2003 | Rath |
| 2004/0057926 | A1 | * | 3/2004 | Ochoa et al. ............... 424/85.1 |
| 2006/0160236 | A1 | | 7/2006 | Morris et al. |

FOREIGN PATENT DOCUMENTS

| EP | 0 441 119 A2 | | 1/1991 |
| JP | 63059899 A | * | 3/1988 |
| WO | WO 99/19295 | | 4/1999 |
| WO | WO 99/43308 | | 9/1999 |
| WO | WO 01/78717 A1 | | 10/2001 |
| WO | WO 01/89519 | | 11/2001 |
| WO | WO 2004/073623 A3 | | 9/2004 |

OTHER PUBLICATIONS

Malgorzata Manteuffel-Cymborowska; Wanda Chmurzyska; Magdalena Peska; and Barbara Grzelakowska-Sztabert."Tumour effect on arginine/ornithine metabolic relationship in hypertrophic mouse kidney" Molecular and Cellular Biochemistry. 1997,168(1-2),51-57.*
Hanzawa, K, et al "Relation between ARGase Type and BA System of Free Amino Acid Type and Concentrations of Arginine and Ornithine in Horse Erythrocytes" Jpn. J. Zootech. Sci., 1986, 57(9), 758-764.*
Albina et al., Role of ornithine as a proline precursor in healing wounds. J Surg Res, Jul. 1993;55(1):97-102.
Blomqvist et al., Enhanced pneumonia resolution by inhalation of nitric oxide? Acta Anaesthesiol Scand. Jan. 1993;37(1):110-4.
Boucher et al., Nitric oxide biosynthesis, nitric oxide synthase inhibitors and arginase competition for L-arginine utilization. Cell Mol Life Sci. Jul. 1999;55(8-9):1015-28.
Bugge et al., Nitric oxide in the treatment of fulminant pulmonary failure in a young pregnant woman with varicella pneumonia. Eur J Anaesthesiol. Apr. 2000;17(4):269-72.
Busch-Petersen et al., [Inhalations with L-arginine in the treatment of cystic fibrosis (author's transl)] Z Erkr Atmungsorgane. May 1975;143(2):140-7. German (English Abstract Considered).
Busse et al., Asthma. N Engl J Med. Feb. 1, 2001;344(5):350-62.
Chambers et al., Effect of nebulised L- and D-arginine on exhaled nitric oxide in steroid naive asthma Thorax. Aug. 2001;56(8):602-6.
Deyun et al., [Protective and treated effects of L-arginine on hypoxia-induced pulmonary hypertension in rats] Hua Xi Yi Ke Da Xue Xue Bao. Mar. 1996;27(1):68-70. Chinese. (English Abstract 70 of reference).
Creager et al., L-arginine improves endothelium-dependent vasodilation in hypercholesterolemic humans. J Clin Invest. Oct. 1992;90(4):1248-53.
De Gouw et al., Effect of oral L-arginine on airway hyperresponsiveness to histamine in asthma. Thorax, Nov. 1999:54(11):1033-5.
Demougeot, at al., Arginase inhibition reduces endothelial dysfunction and blood pressure rising in spontaneously hypertensive rats, Journal of Hypertension, 2005, vol. 23, No. 5, pp. 971-978.

(Continued)

Primary Examiner—Christopher R Tate
Assistant Examiner—Aaron J Kosar
(74) Attorney, Agent, or Firm—Paula A. Borden; Carol L. Francis; Bozicevic, Field & Francis LLP

(57) ABSTRACT

The invention features methods and compositions for diagnosis and treatment of conditions associated with decreased nitric oxide bioavailability, such as a condition associated with elevated arginase activity, using an arginine- and/or arginase-inhibitor based therapy, which therapies include administration of arginine or an arginase inhibitor, either alone or in combination. The invention also contemplates administration of magnesium with arginine, an arginase inhibitor, or with arginine-arginase inhibitor combination therapy. The invention also features methods and compositions for diagnosis, including prognosis, of conditions associated with arginase activity by assessing the ratio of arginine to ornithine in samples from a subject.

12 Claims, 5 Drawing Sheets

OTHER PUBLICATIONS

Demiryurek et al., Peroxynitrite: a putative cytotoxin. Pharmacol Toxicol. Mar. 1998;82(3):113-7.

Dias-Da-Motta et al., The release of nitric oxide and superoxide anion by neutrophils and mononuclear cells from patients with sickle cell anaemia. Br J Haematol. May 1996;93(2):333-40.

Drexler et al., Correction of endothelial dysfunction in coronary microcirculation of hypercholesterolaemic patients by L-arginine. Lancet. Dec. 21-28, 1991;338(8782-8783):1546-50.

Dweik The promise and reality of nitric oxide in the diagnosis and treatment of lung disease. Cleve Clin J Med. Jun. 2001:68(6):486, 488, 490, 493.

Elias et al., Airway remodeling in asthma. J Clin Invest. Oct. 1999;104(8):1001-6.

Elias et al., New insights Into the pathogenesis of asthma. J Clin Invest. Feb. 2003;111(3):291-7.

Endo et al., Induction of arginase I and II in bleomycin-induced fibrosis of mouse lung. Am J Physiol Lung Cell Mol Physiol. Aug. 2003;285(2):L313-21. Epub Apr 4, 2003.

Folkerts et al., Virus-induced airway hyperresponsiveness in guinea pigs is related to a deficiency in nitric oxide. J Clin Invest. Jan. 1995;95(1):26-30.

Gaston et al., The biology of nitrogen oxides in the airways. Am J Respir Crit Care Med. Feb. 1994;149(2 Pt 1):538-51.

Gianetti et al., Inhaled nitric oxide: more than a selective pulmonary vasodilator. Eur J Clin Invest. Aug. 2002;32(8):628-35.

Gladwin et al., Nitric oxide therapy in sickle cell disease. Semin Hematol. Oct. 2001:38(4):333-42.

Gurkan et al, Intravenous magnesium sulphate in the management of moderate to severe acute asthmatic children nonresponding to conventional therapy. Eur J Emerg Med. Sep. 1999;6(3):201-5.

Haas et al, Nitric oxide further attenuates pulmonary hypertension in magnesium-treated piglets. Pediatr Int. Dec. 2002;44(6):670-4.

Hamid et al., Lancet Induction of nitric oxide synthase in asthma. Lancet. Dec. 18-25, 1993;342(8886-8887):1510-3.

Ho et al., Nitric oxide and prostacyclin in acute interstitial pneumonia. J R Soc Med. Jan. 2002;95(1):35-7.

Hoehn et al Treatment of respiratory failure with inhaled nitric oxide and high-frequency ventilation in an infant with respiratory syncytial virus pneumonia and bronchopulmonary dysplasia. Respiration. 1998;65(6):477-80.

Hughes et al, Use of isotonic nebulised magnesium sulphate as an adjuvant to salbutamol in treatment of severe asthma in adults: randomised placebo-controlled trial., Lancet. Jun. 21, 2003;361(9375):2114-7.

Inselman et al., Alterations in plasma amino acid levels in children with asthma: a preliminary investigation. Pediatr Pulmonol. May-Jun. 1986;2(3):163-9.

Jean et al., Beneficial effects of nitric oxide inhalation on pulmonary bacterial clearance. Crit Care Med. Feb. 2002;30(2):442-7.

Jorens et al., "L-arginine-dependent nitric oxide synthase: a new metabolic pathway in the lung and airways." Eur Respir J. Feb. 1993:6(2):258-66.

Kam et al., Nitric oxide: basic science and clinical applications. Anaesthesia. Jun. 1994;49(6):515-21.

Kannan et al., Nitric oxide: biological role and clinical uses, Indian J Pediatr. May-Jun. 1998;65(3):333-45.

Kershenobich et al The relationship between the free pool of proline and collagen content in human liver cirrhosis. J Clin Invest. Dec. 1970;49(12):2246-9.

Kharitonov et al., Increased nitric oxide in exhaled air of normal human subjects with upper respiratory tract infections. Eur Respir J. Feb. 1995;8(2):295-7.

Kimura et al., Measles pneumonia: treatment of a near-fatal case with nitric oxide inhalation. Pediatr Int. Aug. 2002;44(4):451-2.

Knight et al., The lung in sickle cell disease. Pediatr Putmonol. Sep. 1999;28(3):205-16.

Lerman et al., Long-term L-arginine supplementation improves small-vessel coronary endothelial function in humans. Circulation. Jun. 2, 1998;97(21):2123-8.

Lopes Da Mata et al., 1998. How does nitrates in blood correlated to exhaled levels in asthma? European Respiratory Conference, Geneva, Switzerland.

Luiking et al., "Sepsis: an arginine deficiency state?" Crit Care Med. Oct. 2004;32(10):2135-45.

Maxwell et al., Cardiovascular effects of L-arginine. Current Opinion in Nephrology & Hypertension. 7(1):63-70, Jan. 1998.

Meurs et al., "Arginase and asthma: novel insights into nitric oxide homeostasis and airway hyperresponsiveness." Trends Pharmacol Sci. Sep. 2003;24(9):450-5.

Meurs et al., Deficiency of nitric oxide in polycation-induced airway hyperreactivity. Br J Pharmacol. Feb. 1999; 126(3):559-62.

Meurs et al., Increased arginase activity underlies allergen-induced deficiency of cNOS-derived nitric oxide and airway hyperresponsiveness. Br J Pharmacol. Jun. 2002;136(3):391-8.

Meurs et al., Modulation of cholinergic airway reactivity and nitric oxide production by endogenous arginase activity. Br J Pharmacol. Aug. 2000;130(8):1793-8.

Minter et al., Pulmonary complications of sickle cell anemia. A need for increased recognition, treatment, and research. Am J Respir Crit Care Med. Dec. 1, 2001;164(11):2016-9.

Moncada et al., The L-arginine-nitric oxide pathway. N Engl J Med. Dec. 30, 1993;329(27)2002-12.

Mori et al., 2000. Relationship between arginase activity and nitric oxide production. In L. lgnarro, editor. Nitric Oxide. Biology and Pathology. Academic Press, San Diego. 199-208.

Mori et al., Regulation of nitric oxide production by arginine metabolic enzymes. Biochem Biophys Res Commun. Sep. 7, 2000;275(3):715-9.

Morris 2000. Regulation of arginine availability and its impact on NO synthesis. Nitric Oxide Biology and Pathobiology. Academic Press, San Diego. 187-197.

Morris et al., Elevated arginase activity and limited arginine bioavailability: A common feature of asthma and sickle cell disease. Blood 2003; 102:764a (abst 2819).

Morris et al., Arginine therapy: a novel strategy to induce nitric oxide production in sickle cell disease.Br J Haematol. Nov. 2000;111(2):498-500.

Morris et al., Decreased L-arginine bioavailability and elevated arginase activity in sickle cell disease: A novel pathway towards pulmonary hypertension? Blood 2003;102:763a (abstr2818).

Morris et al., Erythrocyte arginase release during hemolysis contributes to endothelial dysfunction and pulmonary hypertension, 27th Annual Meeting of the National Sickle Cell Disease Program, Los Angeles, CA; Apr. 2004.

Morris et al., 2002. Elevated serum arginase activity in patients with sickle cell disease and pulmonary hypertension.. The 30th Anniversary of the National Sickle Cell Program, Washington, DC.

Morris et al., Arginine therapy: a new treatment for pulmonary hypertension in sickle cell disease? Am J Respir Crit Care Med. Jul. 1, 2003;168(1):63-9. Epub Mar. 5, 2003.

Morris et al., Patterns of arginine and nitric oxide in patients with sickle cell disease with vaso-occlusive crisis and acute chest syndrome. J Pediatr Hematol Oncol. Nov.-Dec. 2000;22(6):515-20.

Morris Regulation of enzymes of the urea cycle and arginine metabolism. Annu Rev Nutr. 2002;22:87-105. Epub Jan. 4, 2002.

Morris et al., Dysregulated arginine metabolism, hemolysis-associated pulmonary hypertension, and mortality in sickle cell disease, JAMA, 2005, vol. 294, No. 1, pp. 81-90.

Morris et al., Hydroxyurea and arginine therapy: impact on nitric oxide production in sickle cell disease. Journal of Pediatric Hematology/Oncology, 2003, vol. 25, No. 8, pp. 629-634.

Morris et al., Decreased arginine bioavailability and increased serum arginase activity in asthma, Am J. Respir Crit Care Med. 2004, vol. 170, pp. 148-153.

Nagaya at al., Short-term oral administration of L-arginine improves hemodynamics and exercise capacity in patients with precapillary pulmonary hypertension. Am J Respir Crit Care Med. Mar. 2001;163(4):887-91.

Nakagawa et al., Life-threatening status asthmaticus treated with inhaled nitric oxide. J Pediatr. Jul. 2000;137(1):119-22.

Nathan et al., Reactive oxygen and nitrogen intermediates in the relationship between mammalian hosts and microbial pathogens. Proc Natl Acad. Sci U S A. Aug. 1;97(16):8841-8.

Nijkamp et al., Arch Nitric oxide and bronchial hyperresponsiveness. Arch Int Pharmacodyn Ther. Jan.-Feb. 1995;329(1):81-96.

Palmer et al., Nitric oxide release accounts for the biological activity of endothelium-derived relaxing factor. Nature. Jun. 11-17, 1987;327(6122):524-6.

Pandhi et al, Effect of oral magnesium supplementation on experimental pre-eclampsia induced by prolonged blockade of nitric oxide synthesis in pregnant rats. Indian J Exp Biol. Mar. 2002;40(3):349-51.

Patole et al., Experimental and clinical effects of magnesium infusion in the treatment of neonatal pulmonary hypertension. Magnes Res. Dec. 1995;8(4):373-88.

Perrine et al., A short-term trial of butyrate to stimulate fetal-globin-gene expression in the beta-globin disorders. N Engl J Med. Jan. 14, 1993;328(2):81-6.

Pieper Review of alterations in endothelial nitric oxide production in diabetes: protective role of arginine on endothelial dysfunction. Hypertension. May 1998;31(5):1047-60.

Rees et al., The metabolites of nitric oxide in sickle-cell disease. Br J Haematol. Dec. 1995;91(4):834.

Ricciardolo et al., Randomised double-blind placebo-controlled study of the effect of inhibition of nitric oxide synthesis in bradykinin-induced asthma Lancet. Aug. 10, 1996;348(9024):374-7.

Rossaint et al., Inhaled nitric oxide: its effects on pulmonary circulation and airway smooth muscle cells. Eur Heart J. Nov. 1993;14 Suppl 1:133-40.

Sanders et al., Nitric oxide in asthma. Pathogenic, therapeutic, or diagnostic? Am J Respir Cell Mol Biol. Aug. 1999;21(2):147-9.

Sapienza et al., Effect of inhaled L-arginine on exhaled nitric oxide in normal and asthmatic subjects. Thorax. Mar. 1998;53(3):172-5.

Solomons et al., The use of buffered L-arginine in the treatment of cystic fibrosis. Pediatrics. Feb. 1971;47(2):384-90.

Solomons et al., L-arginine, the sickling phenomenon, and cystic fibrosis. Pediatrics. Jun. 1972;49(6):933.

Takano et al., Oral administration of L-arginine potentiates allergen-induced airway inflammation and expression of interleukin-5 in mice. J Pharmacol Exp Ther. Aug. 1998;286(2):767-71.

Tanaka et al., The effect of allergen-induced airway inflammation on airway remodeling in a murine model of allergic asthma. Inflamm Res. Dec. 2001;50(12):616-24.

Teragawa et al., Mechanisms responsible for vasodilation upon magnesium infusion in vivo: clinical evidence. Magnes Res. Dec. 2002;15(3-4):241-6.

Vercelli, Arginase: marker, effector, or candidate gene for asthma. J Clin Invest. Jun. 2003;111(12):1815-7.

Volpe et al, The role of magnesium in the endothelial dysfunction caused by global ischemia followed by reperfusion: in vitro study of canine coronary arteries. Scand Cardiovasc J. Sep. 2003;37(5):288-96.

Waugh et al., Evidence that L-Arginine is a key amino acid in sickle cell anemia: Nutritional Research 1999; 19:501-518.

Xia et al., Nitric oxide synthase generates superoxide and nitric oxide in arginine-depleted cells leading to peroxynitrite-mediated cellular injury. Proc Natl Acad Sci U S A. Jun. 25, 1996;93(13):6770-4.

Xu et al., Increased arginase II and decreased NO synthesis in endothelial cells of patients with pulmonary arterial hypertension. The FASEB Journal 2004, published on line 9.13.04, pp. 1-23.

Zimmermann et al., "Dissection of experimental asthma with DNA microarray analysis Identifies arginase in asthma pathogenesis." J Clin Invest. Jun. 2003;111(12):1863-74.

Zoritch et al., Nitric oxide and asthma. Arch Dis Child. Mar. 1995;72(3):259-62.

Morris et al. Blood 2002. Arginase Activity is Elevated in Patients with Sickle Cell Disease and Pulomonary Hypertension. 100:452a (abstr 1755, suppl 1).

Schnog et al. Evidence for a Metabolic Shift or Arginine Metabolism in Sickle Cell Disease. Ann Hematol. Jun. 2004;83(6):371-5. Epub Mar. 31, 2004.

Zhang et al. Upregulation of Vascular Arginase in Hypertension Decreases Nitric Oxide-Mediated Dilation of Coronary Arterioles. Hypertension. Oct. 18, 2004. pp. 935-943.

Xu et al. Increase Arginase II and Decreased NO Synthesis in Endothelial Cells of Patients with Pulmonary Arterial Hypertension. and FASEB J. Nov. 2004;18(14):1746-8. Epub Sep. 13, 2004.

Rodriguez et al. How Could Aortic Arginase Activity Enhancement Be Involved in DOCA-Salt Hypertension? Clin Exp Hypertens. Jan. 2004;26(1):1-12.

Lopez et al. L-Arginine Levels are Diminished in Adult Acute Vaso-Occlusive Sickle Cell Crisis in the Emergency Department. British Journal of Haematology. 2003. 120;532-534.

Morris et al. Pattern of L-Arginine and Nitric Oxide Production in SCD Children Hospitalized with Vaso-Occlusive Crisis and Acute Chest Syndrome. Blood 1998. 92:160a (abstr 644, suppl 1).

Morris et al. Effects of L-Arginine Therapy on Nitric Oxide Production in Patients with Sickle Cell Desease. Blood 1998. 92:695a (Abstract 2858).

Morris et al. L-Arginine Therapy Paradoxically Decreases Nitric Oxide Production in Patients with Sickle Cell Disease. Society for Pediatric Research 1999. 45:A876.

Morris et al. Oral Arginine Increases Nitric Oxide Production in Patients with Sickle Cell During Vaso-Occlusive Crisis. Blood 1999. 94:200a (abstract 878, suppl 1).

Morris et al. Nitric Oxide as a Therapeutic Agent in Sickle Cell Disease and Other Vascular Diseases. NIH, Bethesda, Maryland, Sep. 2000; Morris et al. Blood 2000. 96:485a (abstr 2088, suppl 1).

Morris et al. Hydroxyurea and Arginine Therapy: Impact on Nitric Oxide Production in Sickle Cell Disease. Blood 2001; 98:785a(abstract 3262, suppl 1).

Morris et al. A Nitric Oxide Synthase Mechanism for Hydroxyurea? Blood 2001; 98: 487a (abstract 2033, suppl 1).

Morris et al. Arginine Therapy: A new Treatment for Pulmonary Hypertension in Sickle Cell Desease? Nitric Oxide: Biology and Chemistry, 2002; vol. 6, No. 4, pp. 353-496 at abstract at 435.

Morris et al. Hydroxyurea and Arginine Therapy: Impact on Nitric Oxide Production in Sickle Cell Desease. Nitric Oxide: Biology and Chemistry, 2002; vol. 6, No. 4, pp. 353-496 at abstract at 435.

Lopez et al. Is L-arginine, the Substrate for Nitric Oxide, Altered in Adult Vasoocclusive Sickle Cell Crisis? Academic Emergency Medicine. 2002; 9(5):409.

Morris et al. Arginine Therapy Improves Pulmonary Artery Pressures in Patients with Sickle Cell Disease and Pulmonary Hypertension. Blood 2002. 100:452a (abstr 1754, suppl 1).

Lopez et al. Is L-arginine, the Substrate for Nitric Oxide, Altered in Adult Vasoocclusive Sickle Cell Crisis? Blood 2002; 100:452a (abstr 1752, suppl 1).

Styles et al. Oral Arginine Increases Nitric Oxide and Decreases VCAM Production Patients with Acute Chest Syndrome. Blood 2002; 100:452a (abstr 1750, suppl 1).

Morris et al. Arginine Therapy: a Promising New Treatment for Patient with Sickle Cell Disease and Pulmonary Hypertension. J Invest Med 2003;51:S386 (abstr 169, suppl 2).

Morris et al. "Arginine Therapy in Sickle Cell Disease: A Promising New Treatment for Pulmonary Hypertension in Sickle Cell Disease?" Society for Pediatric Research, May 2003.

Featherston et al. Relative Importance of Kidney and Liver in Synthesis of Arginine by the Rat. Am J Physiol. 1973;224:127-9.

Morris et al. "Arginine therapy: a new treatment for pulmonary hypertension in sickle cell disease?" Am J Respir Crit Care Med. Jul. 1, 2003;168(1):63-9. Epub Mar. 5, 2003.

Closs et al. Membrane transport of L-arginine and cationic amino acid analogs. In: Ignarro LJ, ed. Nitric Oxide. Biology and Pathobiology. San Diego: Academic Press; 2000:225-241.

Vallance et al. The Asymmetrical Dimethylarginine/ Dimethylarginine Dimethylaminohydrolase Pathway in the Regulation of Nitric Oxide Genration. Clin Sci. 2001;100:159-60.

Cooke et al. Nitric oxide and vascular disease. Ignarro LJ, ed. Nitric Oxide: Biology and Pathology. New York: Academic Press; 2000:759-783.

Stuhlinger et al. Endothelial Dysfuntion Induced by Hyperhomocyst(e)inemia—role of asymmetric dimethylarginine. Circulation. 2003;108:933-38.

Boger et al. Asymmetric Dimethylarginine, Derangements of the Endothelial Nitric Oxide Synthase Pathway, and Cardiovascular Diseases. Semin Thromb Hemost. 2000;26:539-45.

Ogawa et al. Purification and Properties of a New Enzyme, $N^G$, $N^G$-Dimethylarginine Dimethylaminohydrolase, from Rat Kidney. J Biol Cem. 1989;264:10205-9.

Stuhlinger et al. Homocysteine Impairs the Nitric Oxide Synthase Pathway—Role of Asymmetric Dimethylarginine. Circulation. 2001;104:2569-75.

Graham et al. Plasma Homocysteine as a Rick Factor for Vascular Disease. JAMA. 1997;277:1775-81.

de Jonge et al. Overexpression of Arginase Alters Circulating and Tissue Amino Acids and Guanidino Compounds and Affects Neuromotor Behavior in Mice. J Nutr. 2001;131:2732-40.

Lowenthal et al. Homocysteine Elevation in Sickle Cell Disease. J Am Coll Nutr. 2000;19:608-12.

Wu and Morris. Arginine Metabolism: Nitric Oxide and Beyond. Biochem J. 1998;336:1-17.

Noppen. "Magnesium treatment for asthma: Where do we stand?" Chest, 2002, vol. 122, No. 2, pp. 396-398.

Vichinsky. New therapies in sickle cell disease. The Lancet, Lancet Limited 2002, vol. 360, No. 9333, pp. 639-631.

Yoshihide et al. Prolonged administration of L-arginine ameliorates chronic pulmonary hypertension and pulmonary vascular remodeling in rats. BIOSIS, 1997, XP002422425.

Beale et al., "Early enteral supplementation with key pharmaconutrients improves Sequential Organ Failure Assessment score in critically ill patients with spesis: Outcome of a randomized, controlled, double-blind trial" (2008) Crit. Care Med. 36(1):347.

Reis et al., "Plasma Amino Acid Profile and L-arginine Uptake in Red Blood Cells from Malnourished Uremic Patients" (2006) J. Renal Nutr. 16(4):325-331.

Sandstrom et al., "Serum amino acid profile in patients with acute pancreatitis" (2008) Amino Acids, 35:225-231.

Van Waardenburg et al., "Plasma arginine and citrulline concentrations in critically ill children: strong relation with inflammation" (2007) Am. J. Clin. Nutr. 86:1438-44.

Weinberg et al., "Arginine, nitric oxide, carbon monoxide, and endothelial function in severe malaria" (2008) Curr. Opin. Infect. Dis. 21:468-475.

Scholl-Burgi et al., "Amino Acid Cerebrospinal Fluid/Plasma Ratios in Children: Influence of Age, Gender, and Antiepileptic Medication" (2008) Pediatrics, 121:3920-3926.

Maarsingh et al., "Arginine homeostatis in allergic asthma" European Journal of Pharmacology, (2008) 585:375-384.

* cited by examiner

A. Arginine Levels

B. Arginase Activity

Arginase competes with NOS for L-Arg

TREATMENT AND DIAGNOSIS OF CONDITIONS ASSOCIATED WITH ELEVATED ARGINASE ACTIVITY

CROSS-REFERENCE TO RELATED APPLICATIONS

The present application is a continuation-in-part of PCT application serial no. PCT/US2004/004369, filed Feb. 13, 2004, which application designates the United States and was published in English and which application claims the priority benefit of U.S. provisional application Ser. No. 60/447,373, filed Feb. 14, 2003, each of which applications is incorporated by reference herein in its entirety.

GOVERNMENT RIGHTS

This invention was made with government support under federal grant nos. RR0127119 and HL-04386-01 awarded by the National Institutes of Health. The United States Government may have certain rights in this invention.

FIELD OF THE INVENTION

The present invention is in the field of therapy and diagnosis of conditions associated with elevated arginase as described herein, including asthma, sickle cell disease, and pulmonary hypertension.

BACKGROUND OF THE INVENTION

L-Arginine (Arg) is a conditionally essential amino acid, naturally found in dietary protein. It is converted to nitric oxide (NO) (Palmer et al. Nat Med 1987; 327:524-526; Moncada et al. N Engl J Med 1993; 329:2002-2012; Kam et al. Anaesthesia 1994; 49:515-521) and bronchodilator (Zoritch et al. Arch Dis Child 1995; 72:259-262; Gaston et al. Am J Respir Crit Care Med 1994; 149:538-551), a potent vasodilator, by a family of enzymes known as nitric oxide synthase (NOS). NO is an essential molecule that plays a role in a broad range of functions from vascular regulation, neurotransmission (Moncada et al. 1993, supra), host defense, and cytotoxicity (Nathan et al. Proc Natl Acad Sci 2000; 97:8841-8848) to physiologic control of airways (Gaston et al. 1994, supra). Under conditions of low L-arginine concentration, nitric oxide synthase is uncoupled and reduces oxygen ($O_2$) to superoxide ($O_2^-$) instead of generating nitric oxide (Xia et al. Proc Natl Acad Sci 1996; 93:6770-6774; Dias-Da-Motta et al. Brit J Haematol 1996; 93:333-340). Nitric oxide reacts rapidly with superoxide to form reactive nitric oxide species (RNOS) that could lead to worsening inflammation, oxidative stress and cellular damage (Demiryurek et al. Pharm Toxicology 1998; 82:113-117).

Recently, expression of inducible NO synthase, the enzyme that catalyzes the production of NO from L-Arg, has been found in the epithelium of asthmatic patients but not in healthy non-asthmatic patients (Hamid et al. Lancet 1993; 342:1510-1513: Nijkamp et al. Arch Int Pharmoocodyn 1995; 329:81-96). Asthmatics have exhaled air NO levels that are 3.5 times higher than non-asthmatics, which are correlated with decrease in $FEV_1$ and are affected by therapy Kharitonov et al. Eur Respir J 1995; 8:295-7). Blocking of NO production by L-Arg analogues results in an increase in allergen-induced bronchoconstriction (Ricciardolo et al. Lancet 1996; 348:374-377). A deficiency of NO is involved in airway hyperreactivity (Meurs et al. Br J Pharmacol 1999; 126:559-562). Although asthma is clearly a multifactorial disease, there is some evidence that NO may play an important role in disease pathogenesis (Sanders et al. Am J Respir Cell Mol Biol 1999; 21:147-149). For reviews, see, e.g., Dweik Cleve Clin J Med. 2001 June; 68(6):486, 488, 490, 493; Gianetti et al. Eur J Clin Invest. 2002 August; 32(8):628-35.

Arginase is an enzyme that hydrolyzes Arg to produce ornithine and urea, (Boucher et al. Cell Mol Life Sci 1999; 55:1015-1028) however, in the presence of nitric oxide synthase (NOS), arginine is converted to nitric oxide (NO) and citrulline (Moncada et al. 1993, supra). The expression of arginase can be induced by a variety of cytokines involved in the inflammatory process (Solomons et al. Pediatr 1972; 49:933), particularly the Th2 cytokines. (Mori et al. 2000. Relationship between arginase activity and nitric oxide production. In L. Ignarro, editor. *Nitric Oxide. Biology and Pathology*. Academic Press, San Diego. 199-208.).

Increased serum arginase activities have been reported in patients with SCD at steady-state (Waugh et al. Nutritional Research 1999; 19:501-518.), as well as in an asthma animal model (Meurs et al. Br J Pharmacol 2002; 136:391-398). Arginase activity is elevated in SCD patients with pulmonary disease (Morris et al. Am J Respir Crit Care Med 2003; 168:63-69; Morris et al. 2002. Elevated serum arginase activity in patients with sickle cell disease and pulmonary hypertension. The 30th Anniversary of the National Sickle Cell Program, Washington, D.C.). Plasma arginase activity appears to be related to hemolysis, associated with several markers of hemolytic severity, including LDH (r=0.44, p<0.001), AST (r=0.39, p<0.002), reticulocyte count (r=0.25, p<0.001), and Hct (r=−0.25, p<0.001) (Morris et al, Erythrocyte arginase release during hemolysis contributes to endothelial dysfunction and pulmonary hypertension, $27^{th}$ Annual Meeting of the National Sickle Cell Disease Program, Los Angeles, Calif.; April 2004).

Arginase controls the metabolism of arginine into ornithine, which in turn gives rise to proline and polyamines (Mori et al. 2000, supra; Morris Annu Rev Nutr 2002; 22:87-105; Morris 2000. Regulation of arginine availability and its impact on NO synthesis. Nitric Oxide. Biology and Pathobiology. Academic Press, San Diego. 187-197; Mori et al. Biochem Biophys Res Commun 2000; 275:715-719). These downstream products of arginase activity may play a significant role in the pathogenesis of asthma, pulmonary hypertension and other inflammatory conditions, since proline is involved in collagen formation (Kershenobich et al. J Clin Invest 1970; 49:2246-2249; Albina et al. J Surg Res 1993; 55:97-102) and lung fibrosis (Endo et al. Am J Physiol Lung Cell Mol Physiol 2003; 285:L313-L321), processes that occur in airway wall thickening and airway remodeling (Tanaka et al. Inflamm Res 2001; 50:616-624: Elias et al. J Clin Invest 1999; 104:1001-1006; Elias et al. J Clin Invest 2003; 111:291-297; Busse et al. N Engl J Med 2001; 344:350-362).

Arginine, a safe dietary supplement, has already demonstrated potential for therapeutic utility in several disease processes. (Pieper Hypertension 1998; 31:1047-1060; Lerman et al. Circulation 1998; 97:2123-2128 Perrine et al. N Engl J Med 1993; 328:81-6; Maxwell et al. Current Opinion in Nephrology and Hypertension. 133; Creager et al. J Clin Invest 1992; 90:1248-53; Drexler et al. Lancet 1991; 338:1546-50). In animal studies, inhalation of low doses of L-Arg has completely blocked hyperresponsiveness of reactive airways (Nijkamp et al. 1995, supra; Folkerts et al. J Clin Invest 1995; 94:26-30), and inhaled L-Arg also improves pulmonary functions of cystic fibrosis patients (CF) (Solomons et al. Pediatr 1971; 47:384-390; Solomons et al. Pediatr 1972;

49:933). When tested in a mouse model of allergic asthma, oral administration of L-Arg was reported to aggravate allergen-induced eosinophilic airway inflammation (Takano et al. J Pharmacol Exp Ther 1998 August; 286(2):767-71).

Use of L-Arg is suggested for treatment of cystic fibrosis (Busch-Petersen et al. Z Erkr Atmungsorgane 143:140-7 (1975)); treatment of exercise induced pulmonary hemorrhage in horses (U.S. Pat. No. 6,027,713); and treatment of pulmonary hypertension (U.S. Pat. Nos. 5,217,997; 6,127,421; Nagaya et al. Am J Respir Crit Care Med 163:887-81 (2001); Cheng et al. Hua Xi Yi Ke Da Xue Xue Bao 27:68-70 (1996)).

Use of NO to treat asthma is discussed in Nakagawa et al. J Pediatr. 2000 July; 137(1):119-22; and Rossaint et al. Eur Heart J 1993 November; 14 Suppl I:133-40). The arginase inhibitor N-hydroxy-L-arginine (NOHA) has been tested in a model of asthma (see, e.g., Meurs et al., Br J Pharmacol June 2002, 136(3):391-8, describing administration of an arginase inhibitor in a guinea pig model of allergic asthma; and Meurs et al. Br J Pharmacol 130:1793-8 (2000, describing arginase inhibitors in a perfused guinea pig trachea model)). Use of NO to treat pneumonia has been discussed (see, e.g., Kimura et al. Pediatr Int 2002 August; 44(4):451-2; Ho et al. J R Soc Med 2002 January; 95(1):35-7; Bugge et al. Eur J Anaesthesiol 2000 April; 17(4):269-72; Hoehn et al. Respiration 1998; 65(6):477-80; Blomqvist et al. Acta Anaesthesiol Scand 1993 January; 37(1):110-4; Jean et al. Crit Care Med 2002 February; 30(2):442-7 and Kannan et al. Indian J Pediatr 1998 May-June; 65(3):333-45).

Although early investigators warned of the deleterious impact of nitric oxide in sickle cell disease (SCD) (Knight et al. Pediatr Pulmonol 1999; 28:205-216), more recent studies support its protective function (Gladwin et al. Semin Hematol 2001; 38:333-342). Similar to asthmatic patients (Lopez da Mata et al. 1998. How does nitrates in blood correlated to exhaled levels in asthma? European Respiratory Conference, Geneva, Switzerland.), SCD patients also have elevated $NO_x$ levels at baseline (Rees et al. Br J Haematol 1995; 91:834-7). Serum L-Arg and $NO_x$ levels fall, however, during the vasoocclusive complications of SCD, (Morris et al. J Pediatr Hematol Oncol 2000; 22:515-520) with lowest levels found during acute chest syndrome (pneumonia). Most SCD patients with pulmonary disease have a component of reactive airways that respond to bronchodilators, even though they often do not demonstrate the classical wheezing on physical exam that is usually associated with asthma. Asthma in SCD is often unrecognized and undertreated, and occurs in 30-60% of patients (Minter et al. Am J Respir Crit Care Med 2001; 164:2016-2019). Clinical trials of arginine therapy are now underway for SCD (Morris et al. Brit J Haematol 2000; 111:498-500; Morris et al. 2003, supra).

Magnesium, which can be a dietary supplement, has been described as an adjuvant in combination therapy of asthma with salbumatol (Hughes et al, Lancet 2003; 361:2114-7) or as an asthma intravenous monotherapy (Gurkan et al, Eur J Emerg Med 1999; 6:201-5). Magnesium has also been suggested in infusion therapy of neonatal pulmonary hypertension (Patole et al. Magnes Res 1995; 8:373-88). The effects of oral magnesium in an animal model of pre-eclampsia has been reported (Pandhi et al, Indian J Exp Biol 2002; 40:349-51) and other disease processes that involve endothelial dysfunction (Volpe et al, Scand Cardiovasc J 2003; 37:288-96). Magnesium-induced vasodilation has been reported in animal models of other conditions that involve endothelial-derived nitric oxide (Teragawa et al, Magnes Res 2002; 15:241-6, describing the effects of magnesium in an in vitro canine coronary artery model of endothelial dysfunction). Combined therapy of magnesium and inhaled nitric oxide has shown some promise in an animal model of pulmonary hypertension (Haas et al, Pediatr Int 2002; 44:670-4).

Despite the advances in the field with respect to therapies for conditions such as asthma and sickle cell disease, new therapies are of considerable interest and importance. Furthermore, diagnosis and therapies based upon a more insightful understanding of the underlying mechanisms of these diseases is needed so as to provide a more rationale approach to therapy.

There is a need in the field for improved or alternative therapies for treatment of conditions such as asthma. The present invention addresses these needs.

LITERATURE

U.S. Pat. Nos. 5,217,997; 6,387,890; 4,507,314; 6,359,007; 6,646,006; 6,165,975.

American Society of Hematology Meeting, San Diego December 2003; Morris et al, Blood 2003; 102:763a (abstr2818); Inselman et al. "Alterations in plasma amino acid levels in children with asthma: a preliminary investigation." Pediatr Pulmonol. 1986 May-June; 2(3): 163-9; Jorens et al. "L-arginine-dependent nitric oxide synthase: a new metabolic pathway in the lung and airways." Eur Respir J. 1993 February; 6(2):258-66; Vercelli "Arginase: marker, effector, or candidate gene for asthma" J Clin Invest. 2003 June; 111 (12):1815-7 and Zimmermann et al. "Dissection of experimental asthma with DNA microarray analysis identifies arginase in asthma pathogenesis." J Clin Invest. 2003 June; 111 (12):1863-74 relate to microarray analysis of the expression profiles of lung tissue in two murine models of asthma revealed high levels of arginase I and arginase II activity, in association with IL-4 and IL-13 overexpression. Haas et al, "Nitric oxide further attenuates pulmonary hypertension in magnesium-treated piglets" Pediatr Int 2002; 44:670-4.

Meurs et al. "Arginase and asthma: novel insights into nitric oxide homeostasis and airway hyperresponsiveness." Trends Pharmacol Sci. 2003 September; 24(9):450-5 provides a review in which the authors proposed that a relative deficiency of NO caused by increased arginase activity and altered L-arginine homeostasis is a major factor in the pathology of asthma.

Sapienza et al. "Effect of inhaled L-arginine on exhaled nitric oxide in normal and asthmatic subjects." Thorax. 1998 March; 53(3):172-5 reports that inhaled L-Arg increased exhaled NO in a dose-dependent fashion, with the cumulative effect of L-arginine on NO in asthmatic subjects being significantly higher than in non-asthmatics. This report concluded that L-Arg may have therapeutic potential in diseases in which there is defective production of NO, but in asthma it may amplify the inflammatory response in the airways.

De Gouw et al. "Effect of oral L-arginine on airway hyperresponsiveness to histamine in asthma." Thorax. 1999 November; 54(11):1033-5 concludes that oral L-arginine does not influence airway hyperresponsiveness to histamine as reflected by PC(20), although the dose-response slope is slightly reduced in patients with asthma, thus indicating only marginal, clinically unimportant limitation of NO synthase substrate in asthma.

Chambers et al. "Effect of nebulised L- and D-arginine on exhaled nitric oxide in steroid naive asthma." Thorax. 2001 August; 56(8):602-6. reported that administration of inhaled L-Arg to asthma patients induced bronchoconstriction, with Exhaled NO decreasing with acute bronchoconstriction, and returning to baseline with the resolution of bronchoconstriction. Exhaled NO increased following the administration of both L-arginine and D-arginine.

SUMMARY OF THE INVENTION

The invention features methods and compositions for diagnosis and treatment of conditions associated with decreased nitric oxide bioavailability, such as a condition associated with elevated arginase activity, using an arginine- and/or arginase-inhibitor based therapy, which therapies include administration of arginine or an arginase inhibitor, either alone or in combination. The invention also contemplates administration of magnesium with arginine, an arginase inhibitor, or with arginine-arginase inhibitor combination therapy. The invention also features methods and compositions for diagnosis, including prognosis, of conditions associated with arginase activity by assessing the ratio of arginine to ornithine in a sample from a subject.

The invention is advantageous in that, where the invention contemplates administration of arginine in combination with an arginase inhibitor, the invention can avoid the need to administer higher doses of arginine that may otherwise be needed to treat conditions associated with elevated arginase activity. In short, where elevated arginase increases utilization of arginine, higher doses of arginine would be required to overcome this phenomenon in an arginine monotherapy. Administration of an arginase inhibitor in conjunction with arginine can lower therapeutic dose requirements of arginine. A large dose of arginine, e.g., up to 10 pills, three times a day, that may otherwise be required without combination therapy with an arginase inhibitor is a very large hindrance to achieving therapeutic goals, largely due to poor patient compliance.

Administration of arginine to a patient having elevated arginase levels leads to increased production of ornithine. Plasma ornithine levels strongly correlated to proline levels in asthmatic patients ($r=0.75$, $p<0.0001$, $n=26$). The administration of an arginase inhibitor together with arginine will have the added benefit of decreasing the downstream by-products of ornithine metabolism, e.g., proline and polyamines, both of which are associated with pulmonary and cardiovascular pathology through airway remodeling, lung fibrosis and vascular smooth muscle proliferation. This invention will provide substrate for nitric oxide production, while limiting production of metabolites of arginase activity that would otherwise likely contribute to disease pathology.

Ornithine also decreases arginine bioavailability through competitive inhibition since arginine and ornithine use the same transporter molecules. In short, elevated arginase activity decreases arginine bioavailability. Arginine administered with an arginase inhibitor maximizes arginine bioavailability even in the context of elevated arginase levels.

Still another advantage of the invention is that, compared to administration of arginase inhibitor alone, is that arginase inhibitors are quite expensive. Administration of arginine, which is relatively inexpensive, in conjunction with an arginase inhibitor allows for administration of relatively reduced amounts of expensive arginase inhibitors. In short, administration of arginine and arginase inhibitors will be more effective, and a less expensive therapy.

Another advantage is that the invention avoids the problem that arginine bioavailability remains limited by its low concentration, even in the presence of an arginase inhibitor. Low arginine concentration leads to the uncoupling of nitric oxide synthase (NOS) and superoxide production in lieu of nitric oxide. The Km for arginine transport on the cationic amino acid molecules is around 100 µM; thus reversing the arginine deficiency while maximizing arginine bioavailability and limiting alternate routes of metabolism as per the present invention provide for an improved means for achieving therapeutic goals.

In the context of diagnosis of conditions having elevated arginase activity, the invention is advantageous in that patients can be more accurately diagnosed as to the nature of the disease, whether the disease is amenable to treatment using arginine-based or arginase inhibitor-based therapy, the severity of the disease, and the responsiveness of the patient to therapy.

Where the invention involves assessing elevated arginase activity in a biological sample by assessing the patient's arginine-to-ornithine ratio, the invention also provides the advantage that a simple, relatively inexpensive assay provides a sensitive method of diagnosis of disease, as well as a measure of disease severity.

These and other advantages will be apparent to the ordinarily skilled artisan upon reviewing the present specification.

DEFINITIONS

Figure 1:
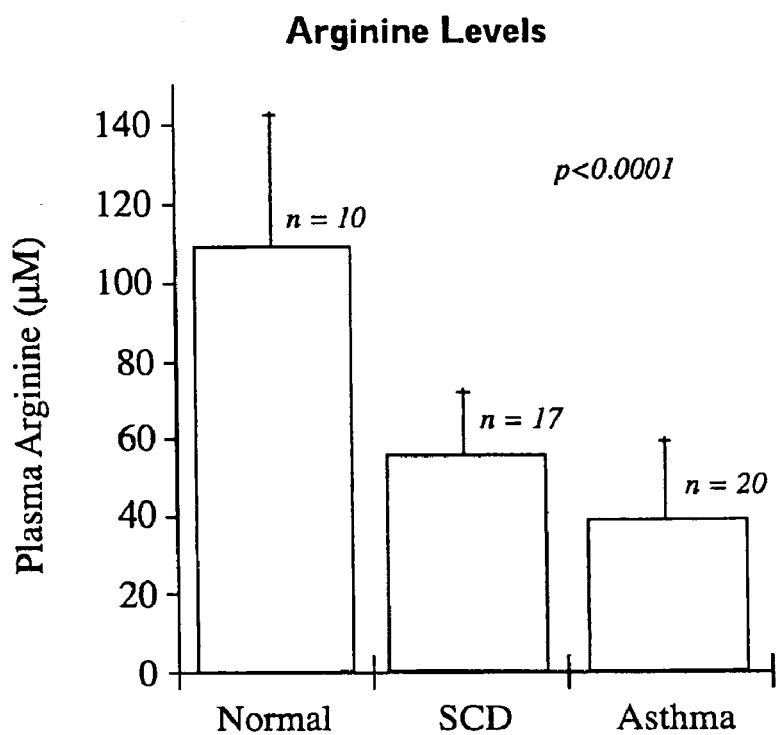
FIG. 1 is a graph showing plasma Arginine concentration (Panel A) and arginase activity (Panel B) in normal non-asthmatic controls (Normal, $n=10$) vs. SCD patients with PHT (SCD, $n=17$), vs. patients with asthma (Asthma, $n=20$). Arginine levels are low and arginase activity is elevated in patients with asthma and in SCD patients with pulmonary hypertension compared to normal controls ($p<0.0001$).
Figure 1:
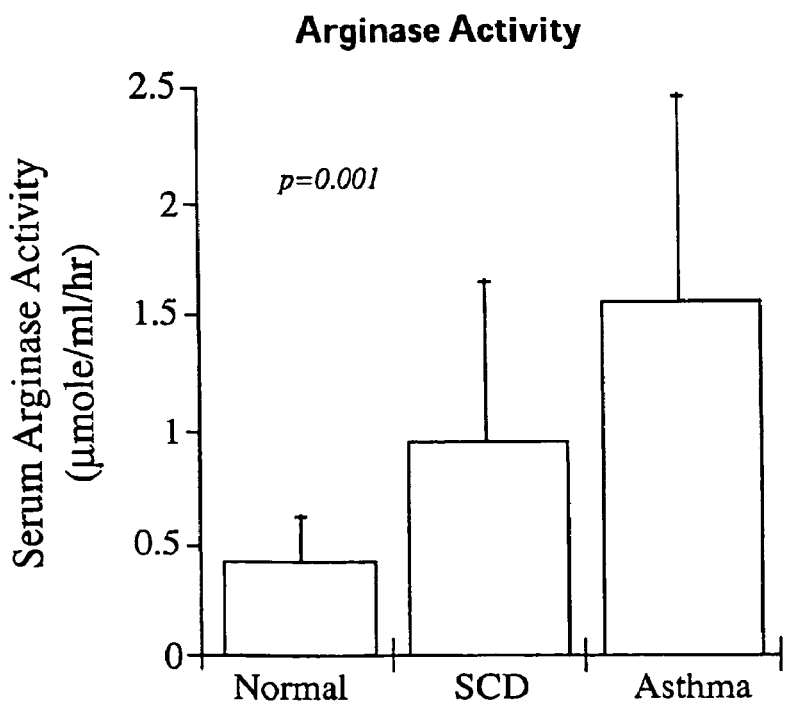

"Arginine" or "Arg" or "L-Arg" as used herein refers to naturally occurring or synthetically produced L-arginine.

"Arginase" as used herein refers to an enzyme that mediates conversion of L-Arg into ornithine and urea, and is meant to encompass any or all relevant arginase types, including, for example, arginase type I, arginase type II, and the like.

"Arginase inhibitor" refers to an agent, such an organic compound or anti-arginase antibody, which agent can be either naturally-occurring or synthetic, which agent affects activity of an arginase (e.g., arginase type I, arginase type II, or both) in catalysis of L-Arg into ornithine and urea. For example, an antibody which binds arginase can affected arginase activity by interfering with arginase binding to its substrate or by promoting clearance of arginase from the subject's circulation. Production of arginase antibodies are well within the skill of the ordinary artisan, and appropriate arginase proteins for production of such antibodies are available.

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment," as used herein, covers any treatment of a disease in a mammal, particularly in a human, and can include: (a) preventing the disease or a symptom of a disease from occurring in a subject which may be predisposed to the disease but has not yet been diagnosed as having it (e.g., including diseases that may be associated with or caused by a primary disease); (b) inhibiting the disease or condition, i.e., arresting its development; and (c) relieving the disease, i.e., causing regression of the disease.

The terms "individual," "host," "subject," and "patient" are used interchangeably herein, and generally refer to a mammal, including, but not limited to, primates, including simians and humans, equines (e.g., horses), canines (e.g., dogs), felines, various domesticated livestock (e.g., ungulates, such as swine, pigs, goats, sheep, and the like), as well as domesticated pets and animals maintained in zoos. Treatment of humans is of particular interest.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "an arginine inhibitor" includes a plurality of such inhibitor compounds and reference to "the arginase" includes reference to one or more arginase polypeptides and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION OF THE INVENTION

The present invention is based on the discovery that arginase plays a role in modifying L-Arg bioavailability in SCD, asthma, pulmonary hypertension, and other pathologic conditions of upregulated arginase activity. Increased arginase activity limits arginine bioavailability through its conversion of L-Arg to ornithine and urea, thereby competing with NOS for available L-Arg substrate and regulating nitric oxide (NO) production. Ornithine itself also decreases L-Arg bioavailability, since both L-Arg and ornithine compete for the same transport system for cellular uptake. Downstream by-products of arginase activity, e.g., proline and polyamines have been implicated in lung and cardiovascular pathology, by way of airway remodeling, fibrosis and vascular smooth muscle proliferation. In addition to decreasing NO bioavailability, elevated arginase activity also provides substrate for a pathway which produces metabolites that likely play a role in the pathogenesis of asthma, pulmonary hypertension and other inflammatory conditions.

There are several possible mechanisms that could lead to increased arginase activity in sickle cell disease. Chronic and acute hemolysis could result in an increased dumping of red blood cell arginase into the circulation. Long-term effects of chronic end organ damage, particularly involving the liver and kidneys, which contain high arginase concentrations, may also lead to leakage of intracellular arginase into the circulation. The inflammatory state of both sickle cell disease and asthma could play a role, as arginase gene expression is upregulated by many cytokines involved in the inflammatory process.

Figure 4:
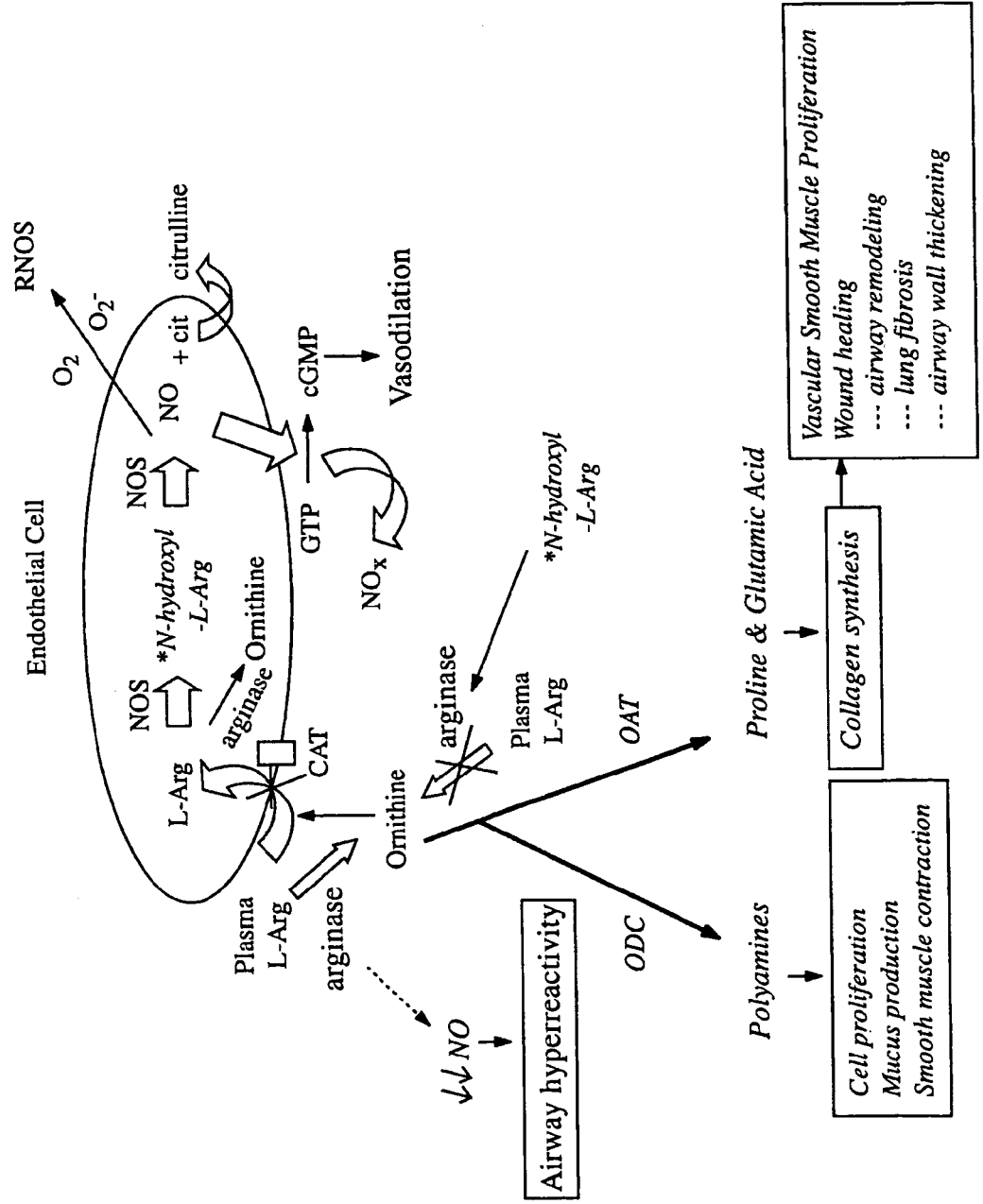
FIG. 4 is a schematic illustrating competition of arginase with nitric oxide synthase for available L-arginine substrate. Downstream by-products of arginase activity are compounds that likely contribute to disease pathogenesis.

Without being held to theory, the present invention is based on the hypothesis that arginase plays a role in modifying L-Arg bioavailability in SCD, asthma, pulmonary hypertension, and other pathologic conditions that involve upregulation of arginase levels/activity. Increased arginase activity limits arginine bioavailability through its conversion of L-Arg to ornithine and urea, thereby competing with nitric oxide synthase (NOS) for available L-Arg substrate and interfering with NO production (FIG. 4). L-Arg produces nitric oxide (NO) and citrulline (cit) in the presence of the nitric oxide synthase enzyme (NOS). Nitric oxide release causes vasodilation through the activation of soluble guanylate cyclase (GTP) to the intracellular messenger cyclic GMP (cGMP). Arginase converts L-arginine to ornithine and urea. Both L-arginine and ornithine use the same Cationic Amino Acid Transporter molecule (CAT) for cellular uptake. Ornithine can competitively inhibit L-arginine transport into the endothelial cell, thereby limiting substrate availability for nitric oxide synthase and regulating nitric oxide production. NG-hydroxyl-L-arginine is the intermediate product of the L-arginine-nitric oxide pathway, and is a potent inhibitor of arginase activity.

Accumulation of both intracellular and extracellular NG-hydroxyl-L-arginine favors the continued conversion of L-arginine to nitric oxide by maintaining adequate arginine availability. The downstream by-products of arginase activity, i.e., proline and polyamines, likely play a role in disease pathogenesis, as they are involved in vascular smooth muscle proliferation as well as airway remodeling (FIG. 4). These metabolites may accumulate in serum or plasma as seen in sickle cell patients with pulmonary hypertension. This is a novel model for the pathogenesis of pulmonary hypertension.

Proline is involved in collagen formation and lung fibrosis, processes that occur in airway wall thickening and airway remodeling. Proline plays an important function in tissue remodeling and normal wound healing, however overproduction can lead to pathologic states. Elevated arginase activity can lead to such conditions.

In an environment of low L-arginine concentration, nitric oxide synthase is uncoupled and reduces oxygen (O2) to superoxide (O2−) instead of generating nitric oxide. Nitric oxide reacts rapidly with superoxide to form reactive nitric oxide species (RNOS) that could lead to oxidative stress and cellular damage. Pathological conditions of increased arginase activity thus have a negative impact on nitric oxide bioavailability. In short, since both arginase and NOS use Arg as a common substrate, arginase plays a role in regulating nitric oxide (NO) synthesis by modulating L-Arg availability. Decreased arginine bioavailability leads to hyperreactive airways in both SCD and asthma, since it plays a role in bronchodilation. Thus, decreased arginine bioavailability and elevated arginase activity contributes to the disease process. Furthermore, decreased arginine bioavailability leads to pulmonary hypertension in the susceptible patient.

Figure 2:
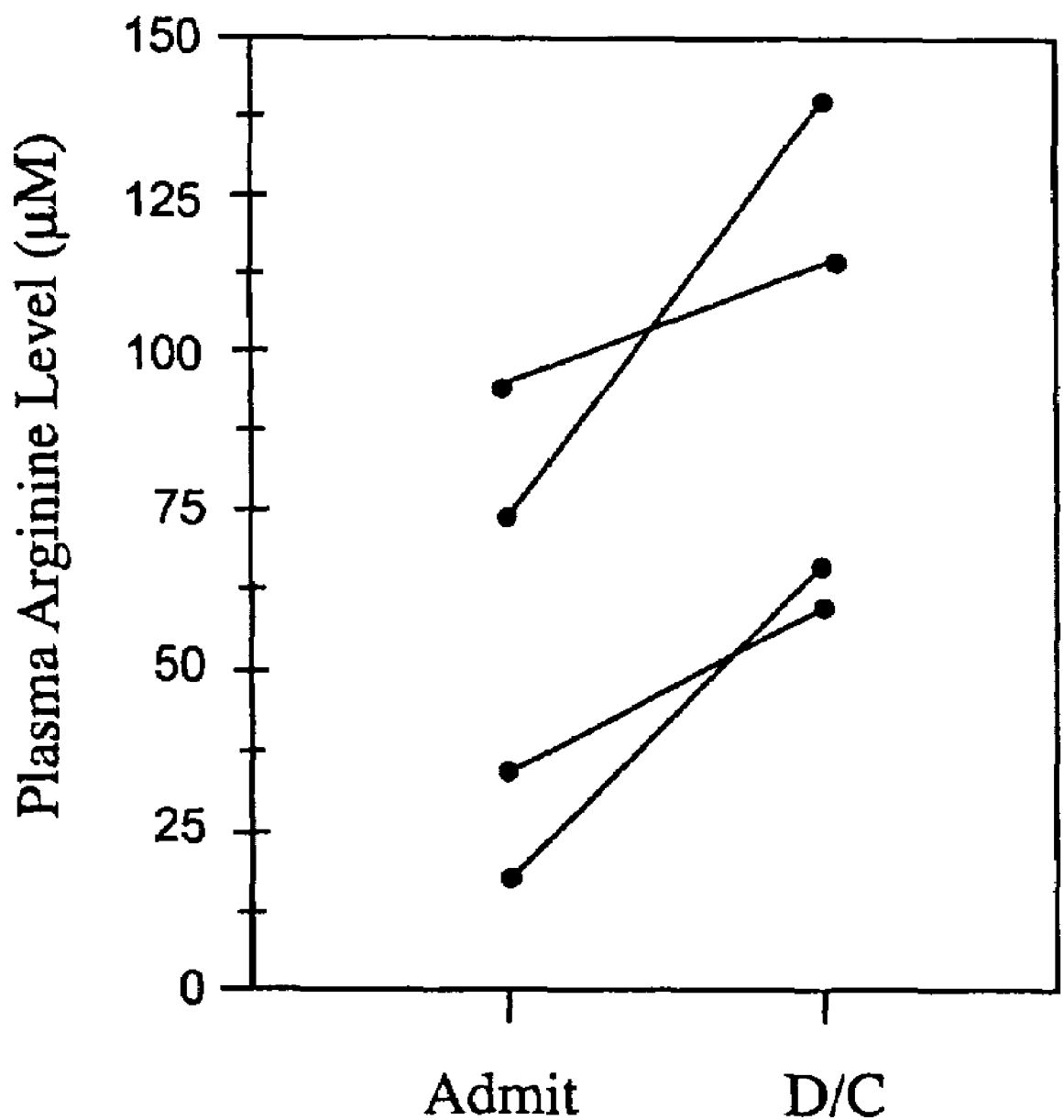
FIG. 2 is a graph showing the change in plasma arginine levels from initial presentation to the emergency department (Admit) vs. the day of hospital discharge (D/C) in asthmatic children (four patients) requiring hospitalization. Low arginine levels rise significantly as clinical condition improved ($p \leq 0.05$).

The data presented herein demonstrate that asthmatic patients exhibit a significant arginine deficiency during acute exacerbations that is even greater than what is observed in patients with SCD (109.0±33.1 vs. 55.4±16.0 vs. 38.9±20 μM in plasma of normal controls vs. SCD patients with pulmonary hypertension vs. asthma, respectively, p<0.0001, FIG. 1, Panel A). Arginine levels rise significantly by discharge in asthmatics admitted to the hospital (FIG. 2). In SCD, this arginine deficiency translates to decreased nitric oxide bioavailability. Arginase activity is elevated in asthmatic patients, (1.6±0.9 vs. 0.95±0.7 vs. 0.427±0.2 μmol/ml/hr, asthma vs. SCD vs. normal controls respectively, p=0.001, FIG. 1, Panel B).

In addition, the inflammatory state of the patient's condition can also play a role, as arginase gene expression is upregulated by many cytokines involved in the inflammatory process, particularly the Th2 cytokines. Data presented herein demonstrates elevated sPLA2 levels in serum of asthmatic patients vs. normal controls (4.2±2 vs. 25.9±30, p<0.05, normal control vs. asthma). Besides the basal cytokine production, the additional increase in the serum and local cytokine levels may be induced by activated lymphocytes, monocytes and other inflammatory cells.

The invention will now be described in more detail.

Arginine and Arginase Inhibitors

Arginine

Arginine as used herein generally refers to L-arginine or "L-Arg". Arginine useful in the invention can be isolated from naturally-occurring sources, provided in an enriched source (e.g., in a foodstuff in which relatively high levels in terms of percent weight is found naturally or is modified to contain such higher levels), or produced by synthetic methods.

L-Arg can be administered as any physiologically acceptable salt, such as the hydrochloride salt, glutamate salt, nitrite, ascorbate etc. L-Arg can also be administered as a peptide (e.g., poly-L-arginine, or combinations of L-Arg and poly-L-arginine). Oligopeptides of particular interest include oligopeptides of from 2 to 30, usually 2 to 20, preferably 2 to 10 amino acids, having at least 50 mol % of L-arginine, preferably at least about 75 mol % of L-arginine, more preferably having at least about 75 mol % of L-arginine. The oligopeptides can be modified by being ligated to other compounds, which can enhance absorption from the gut, provide for enhancement of NO synthesis or stability, e.g. reducing agents and antioxidants, and the like Arginase Inhibitors A variety of arginase inhibitors can be adapted for use in the present invention. The arginase inhibitor can be a reversible or irreversible arginase inhibitor, or arginase antibody. Preferably the arginase inhibitor is compatible for use, or can be adapted so as to be compatible for use, in a pharmaceutically acceptable formulation or in a nutraceutical. Exemplary arginase inhibitors include, but are not necessarily limited to, N(omega)-hydroxy-nor-L-arginine (NOHA), $N^{\omega}$-hydroxy-nor-L-arginine (nor-NOHA), 2(S)-amino-6-boronohexanoic acid (ABH) (see, e.g., U.S. Pat. No. 6,387,890), S-(+)-Amino-6-iodoacetamidohexanoic acid (irreversible); S-(+)-Amino-5-iodoacetamidopentanoic acid (irreversible); L-norvaline, L-HOArg, and the like. NOHA is of particular interest in the present invention.

Magnesium

Without being held to theory, since magnesium has a role in the L-arginine-nitric oxide pathway and attenuates endothelial dysfunction, combination therapy with arginine (with or without an arginase inhibitor) augments the bronchodilatory and vasodilatory properties of magnesium through this pathway. Conditions of associated with decreased nitric oxide bioavailability (e.g., endothelial dysfunction) are amenable to treatment with arginine and magnesium (alone or with an arginase inhibitor). Such combination therapy can have synergistic benefits in treatment of conditions of decreased nitric oxide bioavailability and/or decreased arginine bioavailability.

NO

NO can be administered in a variety of forms, including, but not limited to inhalation, or as a nitric oxide (NO) donor, and the like. NO gas can be inhaled, while NO donors can be administered in a variety of ways according to the nature of the compound, the manner in which it is formulated, and the like. Exemplary NO donors include, but are not necessarily limited to hydroxyurea is an NO donor, sildenafil, nitrite, however there are many agents that are NO donors.

Formulations

L-Arg, arginase inhibitors, magnesium, or other agent for administration according to the invention (referred to herein as "the agents" for convenience) can be formulated in a variety of ways suitable for administration according to the methods of the invention. In general, these compounds are provided in the same or separate formulations in combination with a pharmaceutically acceptable excipient(s). A wide variety of pharmaceutically acceptable excipients are known in the art and need not be discussed in detail herein. Pharmaceutically acceptable excipients have been amply described in a variety of publications, including, for example, A. Gennaro (2000) "Remington: The Science and Practice of Pharmacy," 20th edition, Lippincott, Williams, & Wilkins; Pharmaceutical Dosage Forms and Drug Delivery Systems (1999) H. C. Ansel et al., eds., 7th ed., Lippincott, Williams, & Wilkins; and Handbook of Pharmaceutical Excipients (2000) A. H. Kibbe et al., eds., 3rd ed. Amer. Pharmaceutical Assoc.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

In some embodiments, the agents are formulated separately or in combination, e.g., in an aqueous or non-aqueous formulation, which may further include a buffer (e.g., L-Arg with an arginase inhibitor and/or magnesium, such as L-Arg with an arginase inhibitor, L-Arg with magnesium, L-Arg with both an arginase inhibitor and magnesium, for example). Suitable aqueous buffers include, but are not limited to, acetate, succinate, citrate, and phosphate buffers varying in strength from 5 mM to 100 mM. In some embodiments, the aqueous buffer includes reagents that provide for an isotonic solution. Such reagents include, but are not limited to, sodium chloride, and sugars e.g., mannitol, dextrose, sucrose, and the like. In some embodiments, the aqueous buffer further includes a non-ionic surfactant such as polysorbate 20 or 80.

Optionally the formulations may further include a preservative. Suitable preservatives include, but are not limited to, a benzyl alcohol, phenol, chlorobutanol, benzalkonium chloride, and the like. In many cases, the formulation is stored at about 4° C. Formulations may also be lyophilized, in which case they generally include cryoprotectants such as sucrose, trehalose, lactose, maltose, mannitol, and the like. Lyophilized formulations can be stored over extended periods of time, even at ambient temperatures.

In the subject methods, the agents may be administered to the host using any convenient means capable of resulting in the desired therapeutic effect. In general, administration can be by any suitable parenteral (e.g., intravenous, intramuscular, subcutaneous, and the like) or enteral (e.g., oral) route. Thus, the agents can be incorporated into a variety of formulations for therapeutic administration. More particularly, the agents of the present invention can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols.

In pharmaceutical dosage forms, the agents may be administered in the form of their pharmaceutically acceptable salts, or they may also be used alone or in appropriate association, as well as in combination, with other pharmaceutically active compounds. The following methods and excipients are merely exemplary and are in no way limiting.

The agents can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

For oral preparations, the agents can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents. In some embodiments, particularly in the case of L-Arg, the agents can be formulated in the form of a nutriceutical, e.g., as a food product, e.g., admixed with a foodstuff.

Furthermore, the agents can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature. Agents can also be provided in sustained release or controlled release formulations, e.g., to provide for release of agent over time and in a desired amount (e.g., in an amount effective to provide for a desired therapeutic or otherwise beneficial effect).

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or infusion administration may comprise the inhibitor(s) in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of the agents calculated in an amount sufficient to produce the desired effect in association with a pharmaceutically acceptable diluent, carrier or vehicle. The specifications for the unit dosage forms for use in the present invention depend on the particular compound employed and the effect to be achieved, the pharmacodynamics associated with each compound in the host, and the like.

Dosage forms of particular interest include those suitable to accomplish parenteral (e.g., intravenous, intramuscular, subcutaneous, and the like) or oral administration, as well as dosage forms to provide for delivery by a nasal or pulmonary route (e.g., inhalation), e.g., through use of a metered dose inhaler and the like.

In general, arginine for use in the invention is formulated in either parenteral or enteral forms, usually enteral formulations, more particularly oral formulations. In one embodiment of particular interest, L-Arg is administered in the form of a dietary supplement, which can be provided as, for example, a drink, powdered drink or foodbar. Where the subject has asthma, administration of the agent (e.g., arginine) in an inhaled formulation that is free of irritants, or by a route other than inhalation (e.g., oral or by injection), may be preferred.

Arginase inhibitors for use in the invention are formulated for parenteral administration, e.g., by subcutaneous, intradermal, intraperitoneal, intravenous, or intramuscular injection. Administration may also be accomplished by, for example, enteral, oral, buccal, rectal, transdermal, intratracheal, inhalation (see, e.g., U.S. Pat. No. 5,354,934), etc.

Arginine and arginase inhibitors may be administered as separate dosage forms by the same or different route, or may be formulated as a single dosage form. In one embodiment, arginine and an arginase inhibitor are administered in the form of a capsule, foodbar, or drink, where the two agents may be in separate dosage forms or combined in the same dosage form. In another embodiment, arginine and an arginase inhibitor are provided in the same or different formulation for nebulized delivery. Nebulized delivery may be of particular interest for administration for treatment of asthma and pulmonary hypertension.

Magnesium is generally be administered as a pharmaceutically acceptable magnesium salt, such as, for example, magnesium sulfate, magnesium chloride or the like. Magnesium can be administered as an oral preparation or medicinal food, an intravenous preparation, and/or it can be nebulized as an inhalant. Exemplary dosing for nebulization includes but is not limited to at least about 3 cc (3.2% soln, 95 mg), which can be administered as a one-time dose, a continuous nebulization over one to several hours, or every 5 minutes, 10 minutes, 15 minutes, 20 minutes, 30 minutes, hourly, or other dosing schedule as may be medically indicated (e.g., by a clinical practitioner). Exemplary intravenous dosing includes, but is not limited to, at least about 10 mg/kg to about 500 mg/kg, with exemplary and oral dosing of, for example, at least about 200 gm/day to about 1000 gm/day given as a single dose or divided BID, TID or QID as medically indicated may be used.

Additional Agents for Use in Therapy

In addition to monotherapy or combination therapy of the invention (e.g., involving administration of L-Arg, arginase inhibitor, or both), the invention also contemplates administration of additional agents. In one embodiment of particular interest, nitric oxide (NO) donors, and/or NO in the form of inhaled NO gas, is administered to the subject. For example, in the context of treatment of asthma or other inflammatory conditions having elevated arginase activity, the therapeutic methods of the invention can further include administration of magnesium and/or anti-inflammatory agents such as, for example, phospholipase inhibitors, particularly cytosolic or secretory phospholipase (PLA, e.g., phospholipaseA2 (PLA2)), leukotriene inhibitors, corticosteroids.

Additionally, patients with asthma as well as those with sickle cell disease demonstrate deficiencies in many amino acids. Since extracellular arginine deprivation has been shown to influence intracellular amino acid concentrations, improved arginine bioavailability can serve to normalize some of the aberrant amino acid patterns seen in these disease states. However, combination therapy of other deficient amino acids, such as those indicated as deficient in the examples below, in addition to an agent described herein (e.g., arginine and/or an arginase inhibitor and/or magnesium) can also be beneficial and is included in this invention. Exemplary PLA inhibitors that may be useful are described in U.S. Pat. Nos. 6,492,550; 6,443,001; 6,214,876; 5,641,800; and 5,514,704.

It is well within the skill of the ordinary artisan, given the guidance provided herein, to select a dose and dosage regimen of L-Arg for monotherapy, arginase inhibitor for monotherapy, or L-Arg and arginase inhibitor for combination therapy, any of which can be modified to involve administration of magnesium to provide for a desired therapeutic or otherwise beneficial effect in the subject. Precise doses and dosage regimens can vary with such factors as, for example, whether the agent (e.g., L-Arg, arginase inhibitor) is administered as a monotherapy or in combination with other agents (e.g., as a combination therapy (e.g., L-Arg and arginase inhibitor), with magnesium and/or other agent), subject-dependent factors (e.g., body metrics (e.g., weight, height, size, body surface area, and the like), health, tolerance to agent and/or formulation, and the like); agent-dependent factors (e.g., pharmacokinetics (e.g., including serum half-life), bioavailability, and the like); dosage regimen-dependent factors (e.g., route of administration, course of therapy, and the like); and dosage form-dependent factors (e.g., formulation, bolus dosage form, sustained release dosage form, and the like). In general, L-Arg is administered in a dose of are up to 0.1 g/kg body weight BID (twice daily) to TID (three times daily) with a maximum dose of about 30 gms/day. Lower doses can be administered where arginase inhibitor provides for increased arginine bioavailability, as discussed above. Doses of arginase inhibitor can readily be determined, and in generally are lower amounts than that for arginine.

Methods of Diagnosis and Treatment of Subjects Amenable to Treatment According to the Invention Any subject having a condition associated with decreased nitric oxide bioavailability, such as that which results from decreased arginine bioavailability, elevated arginase (e.g., arginase activity and/or arginase levels), or decreased NO bioavailability are amenable to therapy according to the invention. Such therapies include administration of L-Arg (e.g., as a dietary supplement, etc.), administration of an arginase inhibitor (e.g., NOHA, arginase antibodies), and, in embodiments of particular interest, administration of L-Arg in conjunction with an arginase inhibitor, magnesium, or a combination thereof. For example, magnesium can be administered in conjunction with L-Arg, with arginase inhibitor, or with a combination therapy of L-Arg and arginase inhibitor. Optionally, NO (e.g., in the form of an inhaled gas or NO donor) can be administered in conjunction with L-Arg monotherapy or combination therapy of L-Arg and arginase inhibitor and/or L-Arg and magnesium. The phrase "in conjunction with" contemplates administration of an agent prior to, concurrently, or after other substance or therapy.

The agents (e.g., L-Arg, arginase inhibitor, magnesium, NO) can be administered as separate formulations or, where feasible, as a combined formulation. The agents can be administered at the same time or at different times. Dosages of agents in each of the contexts above can be based upon the various factors as described above. In general, doses may be administered TID (three times a day), BID (twice a day) or QID (four times daily) or QD (daily). For example, the particular regimen for arginase inhibitor (and for arginine) will vary according to a variety of patient factors. For example, where the patient to be treated has sickle cell disease, TID or BID may be of particular interest. For some conditions, such as status asthmaticus, therapy may be administered as a one-time dose in the acute setting, or QD, BID, TID, or QID as deemed medially appropriate.

Exemplary conditions associated with decreased nitric oxide bioavailability and/or elevated arginase levels (relative to non-disease individuals) include, but are not necessarily limited to asthma, sickle cell disease (SCD), pulmonary hypertension (in SCD, neonatal pulmonary hypertension and/or persistent pulmonary hypertension of the newborn, primary hypertension, secondary hypertension), pneumonia, chronic obstructive pulmonary disease (COPD), systemic hypertension, pregnancy related hypertension (pre-eclampsia/eclampsia, arteriosclerosis, diabetes, trauma injury, sepsis, cystic fibrosis, erectile dysfunction, and hemolytic disorders (where the source of elevated arginase activity is via release from the red blood cell, e.g., thalassemia). Conditions amenable to therapy include those that have been previously treated (e.g., as in steroid therapy for asthmatics) or that have not been previously treated ("treatment naïve").

By "elevated arginase activity levels" is meant that the subject exhibits a level of arginase activity that is about 20% greater, usually more than about 20% greater, than arginase activity of an average normal subject. Arginase activity levels can be assessed by direct detection of arginase activity in a sample, or by assessing a ratio of arginine to ornithine amino acids in a sample.

Arginase levels can be assessed in blood (e.g., whole blood or serum, plasma, or other blood fraction), bronchioalveolar lavage, or in target organ tissue samples (e.g., found on biopsy). As used herein "detection of arginase" is meant to encompass detection of arginase protein in a sample, detection of activity of arginase in a sample (either directly or indirectly), or both.

Arginase activity (e.g., in serum or plasma) can be assessed either quantitatively or qualitatively, and may be assessed directly (e.g., by assessing arginase activity or detecting a level of arginase polypeptide) or indirectly (e.g., by assessing a ratio of arginine to ornithine found in blood or other sample). For example, arginase levels can be assessed according to methods well known in the art (see, e.g., Morris et al. Am J Physiol Endocrinol Metab 1998; 275:740-747), by using the methods of the invention involving assessment of arginine and ornithine levels as described herein, or both.

Direct assessment of arginase activity (e.g., by assessing arginase activity or detecting arginase polypeptide) is are a special test that is not routinely available. Specialized laboratories can provide this service. Results can be compared to normal controls (i.e., average arginase levels in patients without an inflammatory condition that might be associated with increased arginase activity). In general, normal, unaffected humans (as reported by Waugh et al, Nutritional Research. 1999. 19; 501-518) demonstrate plasma arginase activity levels of 0.2±0.3 μM/ml/30 min. The present inventor has observed normal serum arginase activity of 0.4±0.2 μM/ml/hr. Thus, arginase activity in plasma and serum of normal controls are low. Levels that are at least about 20% or more above normal are considered elevated. For example, a serum arginase level that is ≧0.6 μM/ml/hr would generally be considered an elevated arginase level. Assessment of arginase activity by assessing a ratio of arginine to ornithine in blood is described in more detail below.

Asthma is a complex syndrome with many clinical phenotypes that involve a multitude of mechanisms, influenced also by genetic and environmental factors. An individual patient's response to asthma therapy also varies, and is likely a reflection of the various mechanisms responsible for disease development and severity. The invention is indicated for those types of asthma that involve elevated arginase activity, decreased arginine bioavailability, and/or limited nitric oxide bioavailability. Included in this group are all varieties of asthma (e.g., allergic asthma, nocturnal asthma, exercise-induced asthma, mild-intermittent, moderate intermittent, moderate persistent, severe persistent, etc). The same is true for the various forms of pulmonary hypertension, and other diseases that manifest with similar clinical symptoms or phenotype but possess underlying mechanistic differences. Altered arginine and nitric oxide bioavailability are likely a common denominator in many of these disease processes, and as such, are amendable to treatment described in this invention.

This invention can be utilized for acute care during exacerbations of the above described conditions, for treatment of the chronic condition, and/or as prophylaxis to avoid development or progression of the described conditions. Many of these conditions have genetic modifiers that have already been identified that put an individual at risk for developing certain diseases, and such techniques (including but not limited to HLA testing, microarray analyses, evaluation of genomic polymorphisms etc) may be helpful in identifying patients who would benefit from this invention.

Assessment of Arginase Levels by Assessing an Arginine-to-Ornithine Ratio in a Patient Sample As noted above, arginase activity in a biological sample of a subject, particularly in a blood sample of a patient (e.g., serum, plasma, or other blood-derived sample), can be assessed based on the arginine-to-ornithine ratio (also referred to herein as the "arginine/ornithine" ratio or "Arg:Orn" ratio). "Biological sample" as used in the context of arginine/ornithine ratio analysis is meant to include any biological sample from a patient (particularly a patient having, at risk of, or suspected of having a condition associated with elevated arginase activity), where the sample is suitable for amino acid content analysis. Exemplary biological samples include, but are not necessarily limited to blood samples (e.g., blood, serum, plasma, and other blood-derived samples), urine, cerebral spinal fluid, bronchioalveolar lavage, and the like.

The arginine/ornithine ratio is a marker of arginase activity and of arginine bioavailability. Arginine bioavailability is limited by elevated plasma ornithine levels through competitive inhibition of cellular uptake of arginine. The present inventor has found that the arginine/ornithine ratio is significantly lower in sickle cell patients, and even lower in sickle cell patients having pulmonary disease (pulmonary hypertension). Likewise, the present inventor has found that the arginine/ornithine ratio is significantly lower in asthmatics, compared to normal controls (0.94±0.5, n=26 vs. 1.6±0.6, n=15, p=0.003). In addition, the present inventor has found arginine/ornithine ratio is lower in subjects having thalassemia compared to normal controls. (0.79±0.4 (n=14) vs. 1.2±0.5 (n=36)). Also, in pulmonary artery hypertension (primary pulmonary hypertension and pulmonary hypertension associated with collagen vascular diseases, n=20) compared to normal controls (0.6±0.4 vs. 1.2±0.5, p<0.001).

This aspect of the invention is based on the discovery that, arginine levels in normal control patients were generally greater than ornithine levels, such that the Arg:Orn ratio often approached 2:1. Such a ratio would avoid a limitation on arginine bioavailability purely on the basis of competitive inhibition, since Arg and ornithine share the same amino acid transporter molecules. However, in subjects affected by a condition having elevated arginase activity (e.g., asthma, pulmonary hypertension, sickle cell disease (SCD), or thalassemia), the ratio of arginine-to-ornithine was significantly decreased.

Without being held to theory, as the ornithine concentration rises, and thus the arginine-to-ornithine ratio decreases, arginine bioavailability becomes limited even under conditions of apparently normal arginine concentration. Pathologically elevated arginase activity reduces the arginine-to-ornithine ratio by utilizing arginine (and decreasing that which is available to nitric oxide synthase to make nitric oxide), while hydrolyzing arginine to ornithine, the substrate for proline and polyamine production, metabolites likely involved in disease pathogenesis A low arginine-to-ornithine ratio, thus, is a reflection of increased arginase activity. Once this ratio nears about 1 or is less than 1, arginine availability for nitric oxide production has reached a competitive disadvantage. An arginine-to-ornithine ratio of less than about 1.2 is considered low and indicative of a condition having elevated arginase activity. Patients with such a finding, regardless of the disease pathology, can be treated with L-Arg monotherapy, arginase inhibitor monotherapy, arginine/arginase inhibitor combination therapy, arginine/magnesium combination therapy, or other therapy of the invention.

A patient having an arginine/ornithine ratio of less than about 1.2 or less than about 1.1 is diagnosed as having a condition in which arginine availability for nitric oxide production is at a competitive disadvantage, and thus the patient is at risk of a condition having elevated arginase activity. In general, a patient having an arginine/ornithine ratio less than or equal to about 1, but greater than about, for example, 0.95, is diagnosed as having a borderline arginine/ornithine ratio and is at risk of developing a condition having elevated arginase activity. A patient having an arginine/ornithine ratio of about or less than about 0.95, 0.8, 0.7, 0.6 or lower is diagnosed as having or at risk for developing a condition having elevated arginase activity.

Diagnosis as to the particular type of condition having elevated arginase can be made based on both the arginine/ornithine ratio in combination with clinical signs and symptoms, generally clinical signs or symptoms that distinguish among conditions associated with elevated arginase. For example, a subject who has sickle cell disease and presents with shortness of breath, decreased exercise tolerance, and a low arginine/ornithine ratio is a candidate for diagnosis of pulmonary hypertension complicating their sickle cell disease. In contrast, a patient who presents with a low arginine/ornithine ratio and cough and/or wheeze is a candidate for diagnosis with asthma. In another example, a patient who presents with a low arginine/ornithine ratio and has a hemolytic disorder like thalassemia is a candidate for diagnosis with pulmonary hypertension. In another example, a patient who presents with a low arginine/ornithine ratio and respiratory symptoms of shortness of breath, and/or decreased exercise tolerance that is not clinically related to asthma is a candidate for diagnosis with pulmonary hypertension and/or pulmonary fibrosis, and likely would benefit from further assessment including, for example, that includes pulmonary function tests and/or Doppler echocardiography.

Other examples of clinical signs or symptoms of conditions identified herein as having elevated arginase are well known to the ordinarily skilled artisan, and the power of the use of arginine/ornithine ratio in combination with such clinical signs and symptoms in diagnosis and differential diagnosis will be readily apparent. In general, the arginine/ornithine ratio provides a tool for the clinician to guide his or her clinical suspicion. In some settings, the arginine/ornithine ratio can be diagnostic where symptoms alone do not point to a definitive diagnosis. For example, with infants and small children a clinical diagnosis of asthma is difficult to make, since many kids cough or wheeze and do not have asthma. However, the arginine/ornithine ratio assessment of the present invention in combination with these symptoms allows the clinician to make a diagnosis of asthma. In providing a test for early diagnosis of asthma or other disease that might otherwise go undiagnosed, the invention avoids the situation where diagnosis is only made after repeated events of clinical signs or symptoms while the underlying cause of the symptoms goes untreated (e.g., repeated events of respiratory symptoms, while inflammation progresses untreated). In the context of asthma, an early diagnosis can avoid the situation where the untreated or maltreated patient develops airway remodeling that could have been avoided if the patient had received early anti-inflammatory treatment (e.g., inhaled steroids, oral steroids, and the like) or a treatment of the invention during the acute exacerbation.

In addition, the a lower the arginine/ornithine ratio may indicate disease severity. A decrease in the arginine/ornithine ratio from an individual's baseline may also reflect disease exacerbation or progression of disease. In addition to its correlation with arginase activity, the arginine/ornithine ratio is a reflection of relative arginine bioavailability, and is influenced by many factors including the body's ability to compensate for low arginine levels through increased intestinal absorption of dietary arginine or increased de novo synthesis from the kidneys (Morris *Biochem J.* 1998; 336:1-17; Featherston et al. *Am J Physiol.* 1973; 224:127-9.) These compensatory mechanisms will help maintain a more normal arginine/ornithine ratio even when arginase activity is elevated.

However compensatory mechanisms may be affected or overwhelmed under certain conditions of disease, or progression of disease, in which case the arginine/ornithine level would decrease. A similar increase in arginase activity may have a greater impact on disease pathogenesis under conditions whereby arginine bioavailability is already compromised, e.g., conditions of renal dysfunction with decrease in de novo arginine synthesis. For example, a patient who presents with an arginine/ornithine ratio of about 0.6, 0.5, 0.4, 0.3, 0.2, or lower has or is at risk of an elevated arginase condition of a greater severity than a patient who presents with an arginine/ornithine ratio of 1.0. In general, an arginine/ornithine ratio that is not equal to or greater than normal but is at least about 75%, 80%, or 85% of the value of normal arginine/ornithine ratio indicates the subject has or is at risk of an elevated arginase condition. If the arginine/ornithine ratio value is more than 25% reduced from the normal arginine/ornithine ratio value, then the subject is diagnosed has having a condition of elevated arginase activity. The lower the arginine/ornithine ratio value relative to a normal arginine/ornithine ratio value, the greater the severity of the disease.

Arginine/ornithine ratios can also be used to assess efficacy of treatment of subject having or at risk of a condition having elevated arginase activity, and further provides a means for rational therapy, including selection of therapy, adjustment of doses or dosage regimen, and the like. In general, therapy is indicated as being efficacious where therapy maintains or increases the arginine-to-ornithine ratio by at least about 5%, 10%, 15%, or 20% or more, with normalization of the arginine/ornithine ratio being a therapeutic goal or endpoint (e.g., to provide for an arginine/ornithine ratio of greater than about 1, preferably greater than about 1.2, 1.3, 1.4, 1.5, or more.

In another embodiment, lysine levels are assessed and the ratio of arginine/(ornithine+lysine) assessed. Since arginine, ornithine and lysine are taken up by cells via the same y+ transport system, the ratio arginine/(ornithine+lysine) provides an index of relative arginine availability at any given plasma arginine concentration. For example, arginine availability as assessed by arginine/(ornithine+lysine) ratio was significantly lower in asthmatic patients as compared to normal controls (0.30±0.13 vs. 0.42±0.14, p<0.005).

In general, a patient having an arginine/(ornithine+lysine) ratio of less than about 0.35 is diagnosed as having a condition in which arginine availability for nitric oxide production is at a competitive disadvantage, and thus the patient is at risk of a condition having elevated arginase activity. A patient having an arginine/(ornithine+lysine) ratio of about or less than 0.3 or lower is diagnosed as having or at risk for developing a condition having elevated arginase activity. Just as with the arginine/ornithine ratio described above, diagnosis of the patient as having or at risk of a particular condition is determined based upon both the arginine/(ornithine+lysine) ratio and clinical signs and symptoms that differentiate between conditions having elevated arginase activity. Arginine and ornithine levels in a patient sample can be assessed according to methods well known in the art. The sample can be any appropriate biological sample obtained from the patient, with a blood sample (e.g., serum, plasma, or other blood-derived sample) being of particular interest.

Calculation of the arginine/ornithine ratio and comparison to a normal arginine-to-ornithine ratio can be performed manually. Alternatively, calculation of the arginine and ornithine levels and diagnosis of a ratio as being normal, borderline or below normal can be partially or fully automated, e.g., using a computer-based system. For example, the arginine and ornithine levels can be entered into a programmed computer, where these data can be entered manually or directly from a device which measures these amino acid levels.

The programmed computer then calculates the arginine/ornithine ratio or amino acid ratios suggestive of global arginine bioavailability (including but not limited to arginine/(ornithine+lysine), optionally, compares the ratio to a normal arginine/ornithine ratio or other amino acid ratios that reflect global arginine bioavailability. Where the program determines the arginine/ornithine ratio is at least equal to or greater than a normal arginine/ornithine ratio, then computer then provides a read out indicating the patient has a normal arginine/ornithine ratio. Where the program determines the arginine/ornithine ratio is at less than or equal to about 1, but greater than about, for example, 0.95, then the computer then provides a read out indicating the patient has a borderline arginine/ornithine ratio and is at risk of developing a condition having elevated arginase activity. Finally, where the program determines the arginine/ornithine ratio is less than 1.0, 0.9, 0.8, 0.7, or lower, then computer then provides a read out indicating the patient has an abnormally low arginine/ornithine ratio, and the patient has or is at risk of developing a condition having elevated arginase activity.

Associated programming for carrying out the computer-based methods of the invention can be recorded on computer readable media (i.e., any medium that can be read and accessed by a computer). Such media include, but are not limited to: magnetic storage media, such as floppy discs, hard disc storage medium, and magnetic tape; optical storage media such as CD-ROMs and DVDs; electrical storage media such as RAM, ROM and EPROM; and hybrids of these categories such as magnetic/optical storage media.

In one embodiment, the programming for carrying out analysis of an arginine/ornithine ratio according to the invention is provided in computer-based system. As used herein, "a computer-based system" refers to a suitable combination of, based on the method to be carried out and how the program is to be provided, a software element, a data storage element, and, optionally, a hardware element, and an output element. The software element provides the programming that, when implemented on a computer, provides for calculation of an arginine/ornithine ratio (and/or other amino acid ratios) and, optionally, comparing the calculated ratio to a normal arginine/ornithine ratio to provide a diagnosis. The data storage element can provide for storage of the program, and optionally storage of data involved in calculating the ratio as well as the result of such calculation. The hardware element provides the means for executing the program, while the display element allows for display of the analysis, particularly the result, to the user. The minimum hardware of the computer-based system generally comprises a central processing unit (CPU), input element, output element, and data storage element. A skilled artisan can readily appreciate that any one of the currently available computer-based system can be programmed to implement the method of the invention, and arc suitable for use in the present invention. The data storage element can comprise any manufacture comprising a recording of the present sequence information as described above, or a memory access means that can access such a manufacture.

Figure 5:
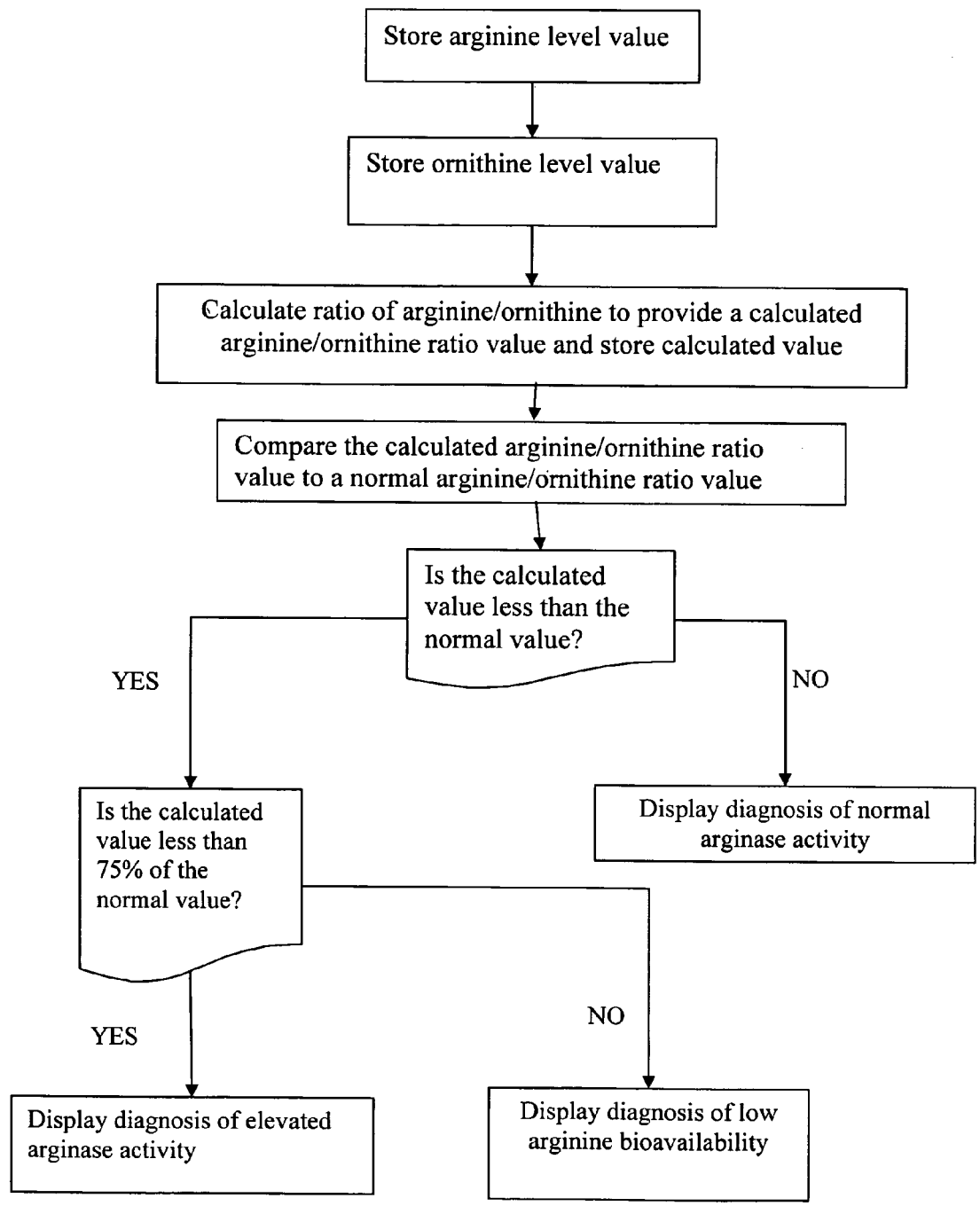
FIG. 5 is an exemplary flowchart of a computer program for assessing arginine/ornithine ratio.

FIG. 5 is an exemplary flowchart of a computer program for assessing an arginine/ornithine ratio. In this example, an arginine level value is stored and an ornithine level value is stored. It is noted that the order in which these values are stored as indicated in FIG. 5 is not meant to be limiting. Although not shown in this example, the arginine and/or ornithine level values are obtained from a sample by a device, which may provide these values for manual entry, or which may provide for automated transfer of the values to the program described herein.

As exemplified in FIG. 5, the ratio of arginine/ornithine is calculated by dividing the arginine level value by the ornithine level value to provide a calculated arginine/ornithine ratio value. The calculated value is then compared to a normal arginine/ornithine ratio value. If the calculated value is not less than the normal value, then a diagnosis of normal arginase activity is made. As illustrated in FIG. 5, this diagnosis can be displayed to the user. If the calculated value is less than the normal value, then the program queries whether the calculated value is at least about 75% of the normal value. If yes, then a diagnosis indicating the subject is at risk of elevated arginase activity is displayed to the user. If no (i.e., the arginine/ornithine ratio value is at least 25% less than an normal arginine/ornithine ratio value), then a diagnosis of elevated arginase activity is displayed to the user.

In another embodiment, the calculated arginine/ornithine ratio value is simply displayed, with the further steps illustrated in FIG. 5 being optional. In another embodiment, the program is modified so as to provide a display that reflects efficacy of a therapy which the patient is receiving. For example, if the calculated arginine/ornithine ratio value is not less than the normal value, then the display can indicate that therapy is efficacious or that arginase activity levels are normalized. As illustrated in this example in FIG. 5, if the calculated arginine/ornithine ratio value is, for example, at least about 75% of the normal arginine/ornithine ratio value, then the display can indicate that elevated arginase activity persists and/or modification or termination of current therapy is advised. If the calculated value is not at least about 75% of the normal value (i.e., the arginine/ornithine ratio value is reduced relative to the normal value by at least about 25% or more), then a display indicating partial or possible efficacy and that modification of therapy (e.g., adjustment of dose or dosage regimen) may be indicated.

Assessing Therapy

Following administration of a therapy according to the invention, efficacy can be assess in the patient by, for example, observing an improvement or stabilization in one or more symptoms relevant to the disease being treated. Therapy can also be assessed by assessing arginase levels, e.g., by assessing arginase activity, e.g., by assessing normalization of the arginine-to-ornithine ratio as described above. Doses of agents administered can be adjusted in accordance to patient need, e.g., to provide for a decrease of arginase activity levels to within a normal range, e.g., within a range such that arginase levels are not above normal levels more than about 5%, 10%, 15%, or 20%, or a sufficient increase in plasma arginine concentration to the extent that arginine bioavailability is no longer limiting factor for nitric oxide production, i.e., levels above the Km for arginine transport (>120 µM), and a normalization of the arginine-to-ornithine ratio (e.g., >1.5).

Therapy can be assessed by examining improvement in one or more clinical symptoms of disease. Successful therapy is normally considered to be a significant improvement in one or more clinical symptoms after treatment according to the invention as compared to prior to such treatment. In some embodiments, an "effective amount" of an agent, e.g., as in an "effective amount" of L-Arg, of arginase inhibitor, or an effective amounts in the context of a combination of L-Arg and an arginase inhibitor, is a dosage that is effective to improve one or more clinical parameters of the condition by at least about 10%, at least about 15%, at least about 25%, at least about 50%, or more, compared to the clinical parameter prior to therapy, or compared with a placebo control or an untreated control. For example, in pulmonary hypertension, clinical parameters assessed can be one or more of: an improvement in mean pulmonary artery systolic pressure as estimated by tricuspid regurgitant jet velocity measured by Doppler-echocardiograpy, improved exercise tolerance as measured by a "6-minute walk"; blood pressure in systemic hypertension, etc).

In the context of conditions that affect lung function, the clinical parameters can be, for example, forced inspiratory flow (FIF), forced expiratory flow (FEF), forced vital capacity (FVC), diffusing capacity for carbon monoxide (DLco), and/or the like. For example, in asthma, therapy can be assessed by spirometry, lung volume, airway resistance, and/or oxygen saturation. In patients having pulmonary hypertension, therapy can be assessed using lung function tests, as well as assessing mean pulmonary artery pressure (e.g., at rest and/or with exercise). It should be noted that successful therapy according to the invention includes outcomes where the underlying disease state is not significantly altered, but one or more clinical symptoms (including symptoms that arise from or are associated with the disease) are treated.

In the context of sickle cell disease, clinical parameters include, for example one or more of: a decrease in the number of pain crisis, number emergency department visits, number of hospitalizations and/or duration of hospitalization, amount of pain medication use, incidence of and/or occurrence of complications such as skin ulcers, need for transfusion, oxygen use, etc. Also improved pain scores and quality of life assessment tools can be followed.

In one embodiment of particular interest, assessment of therapy is by assessing improvement (i.e., increase) in the Arg:Orn ratio of the subject.

Kits

Kits with unit doses of at least one of an L-Arg formulation or an arginase inhibitor formulation, which can be optionally accompanied by a magnesium formulation (which formulations may be combined or separate as described herein) suitable for use in the methods of the invention are provided. In such kits, in addition to the containers containing the unit doses will be an informational package insert describing the use and attendant benefits of the agents in treating conditions associated with elevated serum arginase activity In some embodiments, a subject kit includes a container comprising a formulation comprising a unit dose of L-Arg, an arginase inhibitor, magnesium, or combination thereof, and a pharmaceutically acceptable excipient; and instructions to administer the dosage form according to a desired regimen or exemplary regimen dependent upon the particular condition to be treated, patient age, patient weight, and the like. The instructions can be printed on a label affixed to the container, or can be a package insert that accompanies the container.

In another embodiment, the agents for administration (e.g., L-Arg, arginase inhibitor, magnesium, NO) are provided in the kit along with materials to facilitate analysis of serum arginase levels in the subject who is a candidate for therapy according to the invention.

In other embodiments, the invention contemplates kits having components and instructions for use in assessing arginine and ornithine levels in a subject. In one embodiment, the kit includes a chart to facilitate calculation of the arginine/ornithine ratio and/or for assessing whether the arginine/ornithine ratio is normal, borderline, or indicative of a condition having elevated arginase activity. In another embodiment, the kit includes a handheld device which is preprogrammed to receive the arginine and ornithine level values, calculate the arginine/ornithine ratio and, optionally, provide a readout indicating whether the arginine/ornithine ratio calculated is normal, borderline, or low as described above. The kit may optionally include materials, and the handheld device is programmed to calculate the arginine/(ornithine+lysine) ratio. In another embodiment, the kit includes the materials necessary to determine, e.g., measure, the quantitative levels of arginine and ornithine from the sample provided.

Kits can optionally include instructions for using the components of the kit to practice the subject methods. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric.

Methods and Materials

The following methods, materials, and patient populations relate to those referred to in the Examples 1-3 below.

Asthma patients. Patients with asthma presenting to the emergency department and clinics at Children's Hospital and Research Center at Oakland were recruited. Blood samples and exhaled nitric oxide levels (in patients old enough to perform peak flow) are obtained at presentation to the emergency department or clinic, and followed daily during hospitalization for those patients ill enough to require admission.

Baseline blood was obtained at least 4 weeks after resolution of the acute exacerbation. Blood samples were analyzed for arginine and amino acid levels, arginase activity, and arginine-to-ornithine ratio. Additional analyses that may be performed include analysis of TH-2 cytokines cytokines, VCAM and ICAM, nitric oxide metabolite levels (in blood, breath and urine), genetic markers, IgE, Pla2 levels, RSV (in <2 year old acutely wheezing) and proteomic analysis. A clinical asthma score routinely used at Children's Hospital Oakland, peak flows (when age appropriate) is obtained, and a symptoms questionnaire (see appendix) is filled out on each patient.

Well asthmatics (mild intermittent under good control) and non-asthmatic normal controls will also be recruited for comparison. Wheezing infants who do not carry the diagnosis of asthma will also be recruited for participation in this study in order to determine whether elevated arginase, Th2 cytokines and genetic modifiers can differentiate a subgroup of patients likely to develop asthma (as defined by 3 or greater episodes of wheezing). Follow-up phone calls to these families are done in order to determine repeat episodes of wheezing 1 year after enrollment. A paired student t-test and ANOVA is used for repeated measurements within the same patient, and an unpaired student t-test is used to compare different groups.

Sickle cell patients. Seventeen sickle cell disease patients with documented pulmonary hypertension at steady-state were enrolled in the study. All known patients with pulmonary hypertension receiving care at the Northern California Comprehensive Sickle Cell Center were approached for participation in this analysis. Twelve patients were homozygous for hemoglobin S, three patients had hemoglobin type SC, and two patient had hemoglobin S β-thalassemia. The mean age of patients was 32.7±15 years with a range of 13 to 63 years. There were seven women enrolled. Ten ethnically matched normal non-sickle cell disease volunteers were enrolled as a control group in order to compare amino acid levels and arginase activity. The mean age was 20.6±10 years, ranging from 10 to 34 years. There were four females and six males enrolled. Pulmonary hypertension was defined as estimated pulmonary artery pressures >30 mm Hg by echocardiogram (or tricuspid regurgitant jet velocity of greater than 2.5 m/sec), >two months duration, not associated with acute chest syndrome. A chart review was performed on all patients to obtain tricuspid regurgitant jet velocity data from previous echocardiograms.

Amino Acid Levels. (A complete amino acid panel, including arginine, citrulline, ornithine, and L-arginine analogue asymmetric di-methyl-L-arginine). Quantitative plasma amino acid levels are measured in μmol/L, using a Beckman 6300 amino acid analyzer. The amino acids are separated on an lithium ion exchange column and then reacted with ninhydrin to generate a color response. The data is collected and analyzed using Beckman 32 Karat software, at the Molecular Structure Facility, University of California, Davis, Calif.

Arginase: Arginase-specific activity is determined in plasma by methods previously described. (Morris et al. Am J Physiol Endocrinol Metab 1998; 275:740-747)

NO Analyzer: Serum is stored at −70° until assayed for nitrate/nitrite/S—NO. $NO_x$ can be measured in serum, plasma or urine according to manufacturer's instructions, using Sievers NO Analysis software for liquid sampling (Sievers Instruments, Inc., Denver, Colo.), as previously described. (Waugh et al. Nutritional Research 1999; 19:501-518; Meurs et al. Br J Pharmacol 2002; 136:391-398; Morris et al. 2002. Elevated serum arginase activity in patients with sickle cell disease and pulmonary hypertension. The 30th Anniversary of the National Sickle Cell Program, Washington, D.C.) Briefly, serum nitrite is measured by acidifying serum to a pH <2.0 to convert nitrite to NO. Serum nitrate is measured by incubating serum with Aspergillus nitrate reductase (Boehringer, Mannheim) to reduce nitrate into nitrite and then convert nitrite into NO by the addition of hydrochloric acid. The NO produced is then injected into the NO analyzer (Sievers, Inc), and the NO content of the sample is determined by measuring the luminescence generated in the presence of ozone. The luminescence measured is directly proportional to the amount of NO injected and, in turn, to the nitrite and nitrate content of the samples. Serum samples can be run immediately, or frozen for later analysis.

Exhaled Nitric Oxide: Exhaled nitric oxide is measured in exhaled air, using microprocessor-based chemiluminescent $NO_x$ analytical instrumentation, manufactured by Sievers Instruments, Inc. (Denver, Colo.). The test is easily performed and has been successfully used in many clinical trials. (Hamid et al. Lancet 1993; 342:1510-1513; Morris Annu Rev Nutr 2002; 22:87-105; Morris 2000. Regulation of arginine availability and its impact on NO synthesis. Nitric Oxide. Biology and Pathobiology. Academic Press, San Diego. 187-197) Subjects inhale to total lung capacity from a reservoir bag through a one-way valve (Hans Rudolph, Kansas City, Mo.) with incoming NO-free air to ensure the absence of environmental NO. Next, the subjects exhale to residual volume into the Teflon tube, which enters into the NO analyzer. The subjects exhale at a pressure of +20 mmHg into the tubing connected to the analyzer. Exhalation at this expiratory pressure without a nose clip is a maneuver that closes the velum of the posterior nasopharynx and excludes contamination by nasal NO.

Immunofluorescence staining and flow cytometry (FACS) analysis. Whole blood samples collected into preservative free heparin is used. Monoclonal antibodies used for staining are: FITC conjugated CD3, CD25, CD69, CD80, CD86, CD95 (Immunotech, Westbrook, Me.), PE conjugated CD 154 (CD40L), CD16, CD56, CD63 (Becton Dickinson, San Jose, Calif.), FITC conjugated CD45RA, CD40 (Coulter, Hialeah, Fla.), PE conjugated CD45RO (Beckton-Dickinson, Calif.), PerCP conjugated CD3, CD4, CD8, CD19 (Beckton-Dickinson, San Jose, Calif.). Two- and three-color analyses are performed on the FACScan (BDIS, Mountain View, Calif.). 10,000 events are acquired and analyzed.

T cell activation. Heparinized blood is diluted 1:1 with RPMI and incubated for 8 hours at 37 C with or without the presence of 10 ng/ml of PMA and 1 microg/ml of ionomycin (Sigma Chemical Co.)

Mitogen and antigen blastogenesis. Blood mononuclear cells are stimulated with mitogens or specific antigens to undergo cell division and proliferation. This process is monitored by measurement of thymidine incorporated into newly synthesized DNA within the cells. The mitogen which is used is Phytohaemagglutinin (PHA)(Difco, Detroit), in the working dilutions 1:25, 1:125, 1:625. Antigens will consist of Tetanus Toxoid (Connaught Laboratories Limited, Willowdale, Ontario), Candida (Miles Inc.), cytomegalovirus (CMV), herpes simplex virus (HSV), and varicella-zoster virus (VZV)(Myron J. Levin, M.D. UCHSC, Denver. Colo.). All reactions are run in triplicate with $10^5$ cells plated per well. Incubation time for mitogen assays is 3 days and while that for antigen is 7 days, both at 37° C. in 5% $CO_2$. The cells are pulsed on the last day by adding 50 ul of $^3$H-Thymidine to each well for a final concentration of 1 uCi/well. The plates are harvested 6 to 18 hours after pulsing.

sPLA2: sPLA2 protein is measured using ELISA and sPLA2 activity using breakdown of thioester via methods previously described (Styles et al. Blood 1996; 87:2573-8).

Serum levels of cytokines. We will use frozen serum samples to measure TNF a, sIL-2R, IL-1, IL-2, IL-4, IL-6, IL-10, g-Interferon and CD40L. A commercially available ELISA kit for cytokines is routinely used, according to the manufacturer' instructions (R&D Systems, Minneapolis and Immunotech, Westbrook, Me.). ELISA kits for VCAM, ICAM and levels of sCD40L have recently become available from Chemicon, Calif.

Genetic Markers. NO is synthesized in endothelial cells from L-arginine by the enzyme nitric oxide synthase (NOS) and there are known single nucleotide polymorphisms (SNPs) in the NOS3 gene. Since NO may play a key role in the regulation of bronchomotor tone and inflammation of the airways (Li Current Opinions in Pulmon Med 1997; 3:10-16), genetic studies evaluating the NOS gene in asthmatics may would be of interest. A method for rapidly genotyping multiple SNPs simultaneously has been developed at Roche Molecular Systems, Alameda, Calif. An example of multiplex PCR products is shown in the agarose gel below. These 18 PCR products contain SNPs in genes thought to play a role in asthma: TNFα; CCqα; TNFR1: TNFβ; IL5Rα; TNFβ; IL9; CCR2; IL4Rα; CCR5: RMS1; β2AR; CC16; FcεRIβ; CTLA4; SCYA11; IL4Rα; IL4; and IL6.

Example 1

Analysis of Amino Acid Levels in Asthmatics, Sickle Cell Disease, and PHT Patients Reductions were seen in plasma levels of many amino acids in asthmatic patient experiencing an acute exacerbation of respiratory symptoms (Table 1). Strikingly, the greatest decrease was in plasma levels of arginine, which were approximately half those of normal controls (45±22 μM vs. 94±29 μM; p<0.0001).

TABLE 1

Plasma Amino Acids in Normal Controls vs. Asthma

| Amino Acid | Concentration (μM) | | % Control | p-value |
|---|---|---|---|---|
| | Controls (n = 15) | Asthma (n = 26) | | |
| Arginine | 94 ± 29 | 45 ± 22 | 48 | <0.0001 |
| Ornithine | 64 ± 21 | 49 ± 24 | 77 | NS |
| Citrulline | 30 ± 6 | 21 ± 10 | 70 | 0.002 |
| Proline | 195 ± 66 | 144 ± 73 | 74 | 0.03 |
| Hydroxyproline | 29 ± 14 | 19 ± 9 | 66 | 0.02 |
| Lysine | 162 ± 33 | 112 ± 57 | 69 | 0.004 |
| Glutamic Acid | 55 ± 29 | 40 ± 16 | 73 | 0.04 |
| Glutamine | 554 ± 86 | 466 ± 148 | 84 | 0.04 |
| Glycine | 251 ± 64 | 186 ± 103 | 74 | 0.03 |
| Alanine | 369 ± 104 | 292 ± 96 | 79 | 0.02 |
| Valine | 223 ± 52 | 161 ± 51 | 72 | <0.001 |
| Aspartic Acid | 9 ± 6 | 7 ± 1 | 78 | 0.04 |
| Threonine | 136 ± 29 | 99 ± 58 | 73 | 0.02 |
| Isoleucine | 66 ± 20 | 48 ± 23 | 73 | 0.01 |
| Leucine | 126 ± 32 | 96 ± 45 | 76 | 0.03 |
| Tyrosine | 72 ± 15 | 52 ± 20 | 72 | 0.002 |
| Histidine | 75 ± 10 | 57 ± 20 | 79 | 0.003 |
| Cysteine | 22 ± 13 | 20 ± 16 | 90 | NS |
| Asparagine | 35 ± 15 | 41 ± 18 (n = 25) | 118 | NS |
| Serine | 107 ± 32 | 89 ± 64 | 83 | NS |
| Tryptophan | 45 ± 10 | 37 ± 15 | 82 | NS |
| Methionine | 25 ± 6 | 20 ± 13 | 80 | NS |
| Phenylalanine | 57 ± 13 | 56 ± 17 | 98 | NS |

Concentrations of amino acids are expressed as means ± SD. % Control values reflect percentages of controls for the asthma group.

As arginine, ornithine and lysine are taken up by cells via the same y+ transport system, the ratio arginine/(ornithine+lysine) provides an index of relative arginine availability at any given plasma arginine concentration. Relative arginine availability also was significantly lower in asthmatic patients as compared to normal controls (0.30±0.13 vs. 0.42±0.14, p<0.005), further limiting arginine availability in the asthma group.

Plasma levels of ornithine (Table 1), a product of arginine catabolism, were generally lower in asthmatics relative to controls, and relative ornithine availability (ornithine/(arginine+lysine)) was somewhat higher in asthmatics than in controls (0.25±0.07 for controls, 0.34±0.17 for asthma), but neither of these trends reached statistical significance. On the other hand, citrulline, the precursor of endogenous arginine synthesis, was significantly reduced in asthmatics relative to normal controls (Table 1), possibly contributing to the decrease in plasma arginine levels in these patients.

Table 2 shows plasma amino acids in normal controls vs. patients with sickle cell disease (SCD). An abnormal amino acid profile is found in patients with sickle cell disease. The greatest deficiency is found in plasma arginine concentration.

TABLE 2

Plasma Amino Acids in Normal Controls vs. SCD

| Amino Acid | Concentration (μM) | | % Control | p-value |
|---|---|---|---|---|
| | Controls (n = 29) | SCD (n = 163) | | |
| Nonessential: | | | | |
| Arginine | 65 ± 16 | 40 ± 15 | 62 | <0.0001 |
| *Ornithine | 61 ± 22 | 64 ± 23 | — | NS |
| *Citrulline | 27 ± 11 | 25 ± 14 | — | NS |
| *Proline | 141 ± 49 | 205 ± 76 | 145 | <0.0001 |
| *Glutamic acid | 38 ± 15 | 47 ± 24 | 124 | 0.04 |
| Glutamine | 515 ± 129 | 607 ± 125 | 118 | 0.0004 |
| Glycine | 205 ± 48 | 278 ± 98 | 136 | 0.0001 |
| Tyrosine | 61 ± 13 | 53 ± 19 | 87 | 0.03 |
| Alanine | 330 ± 69 | 321 ± 110 | — | NS |
| *Cysteine | 40 ± 7 | 45 ± 15 | — | NS |
| Serine | 93 ± 15 | 94 ± 23 | — | NS |
| Asparagine | 44 ± 13 | 43 ± 14 | — | NS |
| Essential: | | | | |
| Lysine | 161 ± 30 | 143 ± 34 | 89 | 0.006 |
| Histidine | 73 ± 15 | 56 ± 16 | 77 | <0.0001 |
| Phenylalanine | 61 ± 13 | 53 ± 19 | 87 | 0.03 |
| *Leucine | 114 ± 25 | 89 ± 28 | 78 | <0.0001 |
| *Valine | 207 ± 41 | 162 ± 45 | 78 | <0.0001 |
| Isoleucine | 58 ± 13 | 49 ± 16 | 84 | 0.008 |
| Methionine | 25 ± 5 | 26 ± 7 | — | NS |
| Threonine | 137 ± 31 | 126 ± 45 | — | NS |

Concentrations of amino acids are expressed as means ± SD.
% Control: Values are shown only when significantly different from controls.
*Amino acids that are altered in SCD patients with PHT vs. SCD patients without PHT Table 3 illustrates plasma amino acid levels that differ in sickle cell disease patients with pulmonary hypertension compared to those without pulmonary hypertension. Elevated downstream by-products of arginase activity occur in SCD patients who have developed pulmonary hypertension.

TABLE 3

Plasma Amino Acids in SCD with PHT vs. SCD with PHT

| Amino Acid | Concentration μM | | | p-value |
|---|---|---|---|---|
| | Controls (n = 29) | TR jet < 2.5 (n = 86) | TR jet ≧ 2.5 (n = 41) | (PHT vs non PHT) |
| Nonessential: | | | | |
| Ornithine | 61 ± 22 | 59 ± 20 | 69 ± 23 | 0.02 (↑) |
| Citrulline | 27 ± 11 | *22 ± 10 | 29 ± 20 | 0.008 (↑) |
| Proline | 141 ± 49 | *192 ± 74 | *236 ± 87 | 0.003 (↑) |
| Glutamic acid | 38 ± 15 | *45 ± 16 | *60 ± 37 | 0.003 (↑) |
| Cysteine | 40 ± 7 | 43 ± 14 | *48 ± 16 | 0.04 (↑) |
| Essential: | | | | |
| Valine | 207 ± 41 | *165 ± 41 | *145 ± 48 | 0.01 (↓) |
| Leucine | 114 ± 25 | *92 ± 25 | *78 ± 30 | 0.006 (↓) |

Concentrations of amino acids are expressed as means ± SD.
*Amino acids that differ significantly (p < 0.05) from controls

Example 2

Arginine and Arginase Levels in Asthmatic Patients and Sickle Cell Disease (SCD) Patients with Pulmonary Hypertension SCD and asthmatic patients exhibited a significant arginine deficiency during acute exacerbations. Serum arginine levels are summarized in the table below, and presented in FIG. 1 (Panel A).

|  | Normal | SCD with PHT | Asthma |
| --- | --- | --- | --- |
| Serum arginine (µM) | 109.0 ± 33.1 | 55.4 ± 16.0 | 38.9 ± 20 |

PHT = pulmonary hypertension; $p < 0.0001$ for comparison of SCD with PHT vs. normal, and for asthma vs. normal.

Arginase activity was elevated in SCD patients with PHT relative to normal controls, and was even greater in asthmatic patients. Serum arginase activity levels are summarized in the table below, and the data presented in FIG. 1 (Panel B).

|  | Normal | SCD with PHT | Asthma |
| --- | --- | --- | --- |
| Serum arginase activity (µmol/ml/hr) | 0.427 ± 0.2 | 0.95 ± 0.7 | 1.6 ± 0.9 |

$p = 0.001$ for comparison of SCD with PHT vs. normal, and for asthma vs. normal.

FIG. 1 (Panel B) is a graph showing arginase activity in normal non-asthmatic controls (Normal, n=10) vs. patients with sickle cell disease and pulmonary hypertension (SCD, n=17) vs. patients with asthma (Asthma, n=20). Arginase activity was significantly increased in patients with asthma compared to normal controls ($p<0.001$). Arginase activity is even higher in asthmatics compared than sickle cell patients with pulmonary hypertension. Two patients with SCD having the highest levels of arginase activity died within 1 year of obtained values. Elevated arginase activity may be a reflection of increased disease severity in sickle cell disease, and is likely an inflammatory marker in asthma that potentially plays a role in disease pathogenesis.

As illustrated in FIG. 2, arginine levels rose significantly by discharge in asthmatics admitted to the hospital ((54.7±29 vs. 93.1±37 µM, $p<0.05$, n=4). Serial arginase activity levels were available on two patients and dropped substantially by discharge in each case (1.85 decreased to 1.12 µmol/ml/hr and 3.86 decreased to 0.50 µmol/ml/hr). It is likely that high arginase activity in asthmatic patients contributes to low circulating arginine levels, thereby limiting arginine bioavailability and creating a nitric oxide deficiency that induces hyperreactive airways.

Figure 3:
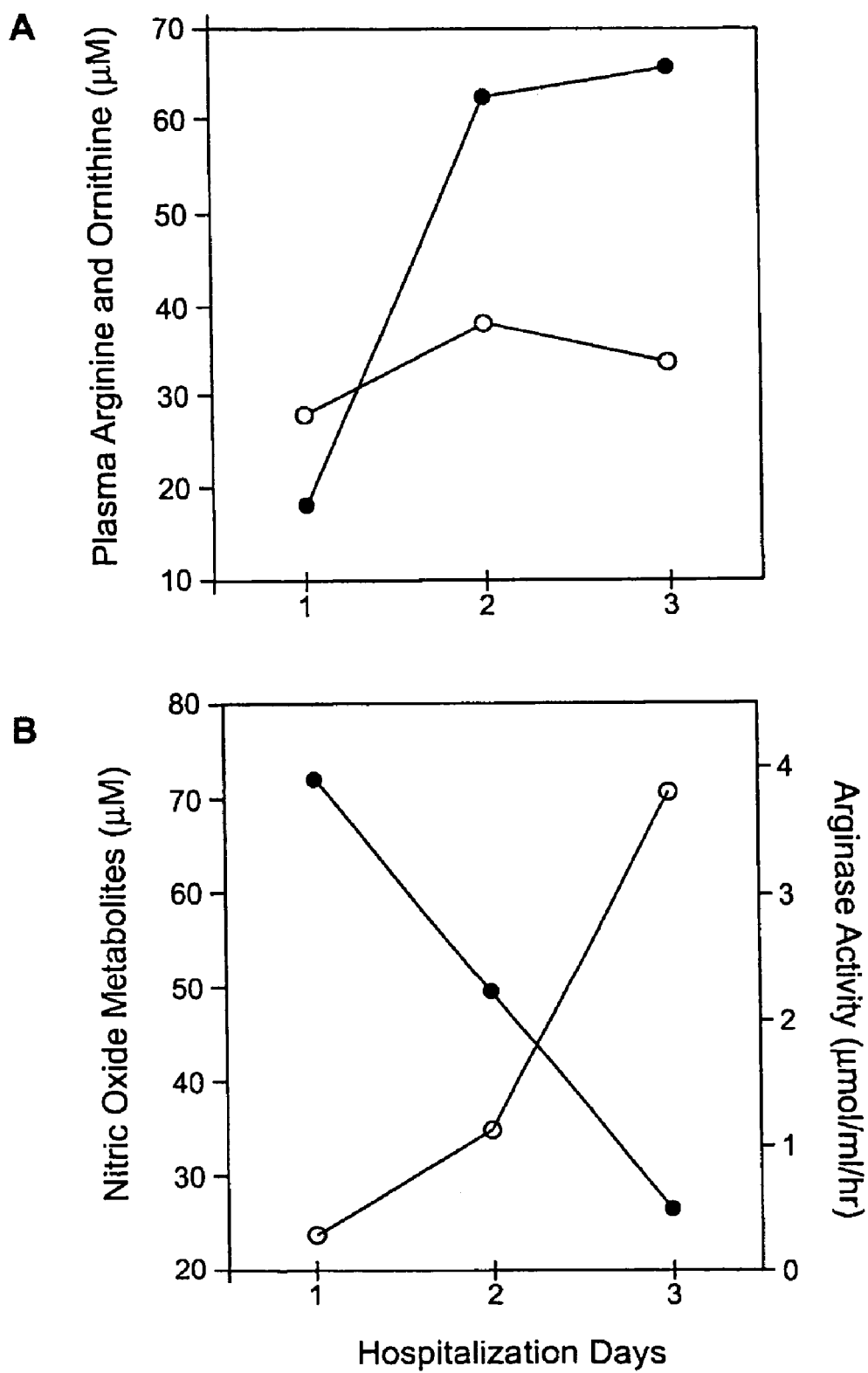
FIG. 3 is a graph demonstrating changes in plasma arginine and ornithine concentration (Panel A; closed circles, arginine levels; open circles, ornithinine levels), arginase activity and nitric oxide metabolites (Panel B; closed circles arginase activity; open circles, serum nitric oxide metabolites (NOx)) during hospitalization in a representation four-year old boy with status asthmaticus.

FIG. 3 represents changes in plasma arginine and ornithine concentration, arginase activity and nitric oxide metabolites during hospitalization in a representation four-year old boy with status asthmaticus. Sequential plasma arginine (filled circles) and ornithine levels (unfilled circles) are followed over a three-day hospitalization. Day "1" is the day of admission, obtained in the emergency department, and day "3" is the day of discharge. As shown in Panel A of FIG. 3, low arginine levels increase significantly during the course of hospitalization, as does the arginine-to-ornithine ratio (0.65, day 1 vs. 1.6, day 2 vs. 1.9, day 3).

As shown in Panel B of FIG. 3, serum nitric oxide metabolites (unfilled circles) and arginase activity (filled circles) are also followed over the three-day hospitalization. Arginase activity dropped dramatically as the patient clinically improved, and reached a normal level by discharge, corresponding to an increase in serum nitric oxide metabolite production. An improvement in arginine and nitric oxide bioavailability occurred as the asthma exacerbation resolves.

In addition, the inflammatory state of the patient's condition can also play a role, as arginase gene expression is upregulated by many cytokines involved in the inflammatory process, particularly the Th2 cytokines. Elevated sPLA2 levels were observed in asthmatic patients vs. normal controls (4.2±2 vs. 25.9±30, $p<0.05$, normal control vs. asthma) in serum. Since phospholipase A2 is a precursor to leukotrienes, elevated sPLA2 may identify patients who would respond to leukotriene inhibitors. Combination therapy of one or more agents described herein with leukotriene inhibitors or sPLA2 inhibitors/antibodies is beneficial for patients with asthma and other inflammatory conditions involving elevated cytokines.

Example 3

Arginase Levels of SCD Patients with PHT After Treatment with Arginine

Patients with sickle cell disease and documented pulmonary hypertension by echocardiography were treated with oral L-arginine-HCl, at a dose of 0.1 g/kg TID for five days. Echocardiograms were performed before and after L-arginine administration, on Day 0 and Day 6, and at $\geq 1$ one month follow-up after completion of arginine therapy. Blood samples for determination of amino acid levels were drawn in the morning of Day 0 (pre-treatment), Day three 3, and Day six of the study. Arginase activity levels were determined on Day 0. No patients were being concurrently treated with vasodilators or anticoagulant agents, and no patients received a red blood cell transfusion during the five-day study period. Cardiologists involved in the interpretation of echocardiograms were unaware of the therapy given.

Echocardiography. Oral L-arginine supplementation significantly reduced pulmonary artery systolic pressure by a mean of 15.2% (63.9±13 to 54.2±12 mmHg, p=0.002) after five days of therapy. One patient was determined to be non-compliant based on plasma L-arginine concentration at the end of the study (61.5 µM/L at Day 0 vs. 44.9 µM/L Day 6). He was the only patient found to not show an improvement in pulmonary hypertension by echocardiogram.

The tricuspid regurgitant jet velocity from echocardiograms obtained >two months prior to study enrollment demonstrated stable estimated pulmonary artery systolic pressures in five 5 patients, and worsening pulmonary hypertension in two patients. Results were unavailable from outside hospitals in three patients. Follow-up echocardiography was obtained at $\geq$one month after arginine therapy in the nine compliant patients, with mixed results. The non-compliant patient was lost to follow-up. Four patients reverted to their previous baseline pulmonary artery systolic pressures, four patients exhibited persistent improvement, and one patient demonstrated a worsening of pulmonary hypertension (echocardiography done while admitted for acute chest syndrome). Two of the patients demonstrating persistent improvement had also been started on transfusion therapy due to the severity of their disease, and one of these two patients had continued arginine therapy (at a dose of 0.1 gm/kg BID).

Amino Acid levels. Plasma L-arginine levels were low in patients with pulmonary hypertension compared to normal controls (50.8±19 vs. 114±27 µM, p<0.0001), but similar to levels found in sickle cell patients at steady-state who did not have pulmonary hypertension. However the arginine-to-ornithine ratio was significantly lower in patients with pulmonary hypertension compared to normal controls (0.95±0.3 vs 2.0±0.6, p<0.0001), suggesting increased arginase activity and decreased arginine bioavailability. Both L-arginine and ornithine concentrations increased significantly after five days of oral L-arginine supplementation (n=10, p<0.05).

Arginase activity. Arginase converts L-arginine to ornithine and urea. Arginase activity in serum was higher in sickle cell patients with pulmonary hypertension compared to normal controls (0.82±0.6 vs. 0.43±0.2 µmol/ml/h). Of interest, the patients with the two highest levels of arginase activity (1.22 and 2.46 µmol/ml/h) have died within one year of enrollment. Elevated arginase activity may be a marker for disease severity.

Example 4

L-Arg and NOHA Combination Therapy

The effect of L-Arg and the arginase inhibitor NOHA, alone and in combination in the treatment of SCD is examined. The effect agents are examined on cell sickling, red cell indices, on functional properties of hemoglobin and on the existence of adverse effects such as hemoglobin oxidation and red cell hemolysis. The effect of the agents on interactions between sickle cells and endothelial cells, membrane transport properties and cell volume control are also examined. In vivo studies are performed using various lines of transgenic mice which produce different levels of Hemoglobin S, including those which produce human Hb S/Hb F exclusively.

Example 5

Arginine Monotherapy and Combination Therapy of Arginine and Magnesium

A randomized, double-blinded placebo-control trial of intravenous arginine or arginine and magnesium for the treatment of status asthmaticus is conducted as follows. Patients with respiratory distress and asthma are recruited from the emergency department or clinics at Children's Hospital Oakland. Study drug is administered as a one-time dose in the emergency department. Arginine or placebo is continued every 8 hours for patients admitted to the hospital. Primary outcome measures are admission vs. discharge patient parameters, and length of hospital stay, improvement in clinical asthma scores and oxygen saturations/need for supplemental oxygen use. Plasma amino acids, arginine-to-ornithine ratio, arginase activity, nitric oxide metabolites (in serum, exhaled breath and urine), PLA2, cytokines, inflammatory biomarkers, genetic modifiers and peak flows are followed.

Example 6

Arginine Monotherapy

Although Chambers et al. "Effect of nebulised L- and D-arginine on exhaled nitric oxide in steroid naive asthma." Thorax. 2001 August; 56(8):602-6. reported that administration of inhaled L-Arg to asthma patients induced bronchoconstriction, with exhaled NO decreasing with acute bronchoconstriction, and returning to baseline with the resolution of bronchoconstriction, similar bronchoconstriction occurred with their control test using an alternate amino acid. It is likely that the acute bronchoreaction was due to irritation of the inhalant itself, rather than arginine. Irritation can be avoided by careful selection of a non-irritating inhalant and/or selection of formulation components that do not cause significant irritation upon inhalation (i.e., a low irritant or non-irritating formulation). Such issues can also be avoided by administration of arginine by a route other than inhalation, e.g., by oral or intravenous administration.

The effects of arginine supplementation on pulmonary function tests is evaluated by administering supplemental arginine (oral or intravenous) alone or in conjunction with magnesium and/or an arginase inhibitor to patients with a known diagnosis of asthma, defined as ≧3 wheezing episodes and a past history of asthma medication usage (e.g., bronchodilators, steroids, inhaled steroids, or leukotriene inhibitors etc). Pulmonary function tests are performed before and after a single dose of arginine (0.1 gram/kg to a max of 10 grams).

One patient has already been enrolled in this study. A single dose of oral arginine (0.1 gm/kg) was administered. Pulmonary function tests were determined prior to treatment and 2 hours after arginine supplementation. Although supplemental arginine did not significantly effect spirometry (except FIF 50%—inducing a 23% improvement), and had minimal effect on lung volumes, treatment had an impressive impact on airway resistance within 2 hours (Raw decreased by 22% and Gaw increased by 28%). Since increased airway resistance is a significant problem during an acute exacerbation of asthma, a benign therapy that decreases airway resistance, likely through smooth muscle relaxation, benefits patients with asthma. Also of interest, the patient's oxygen saturation by venous blood gas increase from 85 to 92%.

Even greater benefits can appreciated after more than 2 hours post treatment or when used in combination with standard of care asthma therapy such as bronchodilators and steroids.

Example 7

Arginine-to-Ornithine Ratio as a Biomarker of Arginase Activity in Sickle Cell Disease The associations between plasma arginase, arginine metabolism and pulmonary hypertension was evaluated in patients having sickle cell disease (SCD). Plasma and erythrocyte arginase activity and amino acid levels were determined for patients with SCD and compared to ethnically matched control subjects. A diagnosis of pulmonary hypertension (PHT) by Doppler-echocardiogram and prospective mortality were determined over 30 months of sequential patient enrollment.

Plasma arginase activity was significantly elevated in patients with SCD compared to controls (2.2±2, n=140 vs. 0.4±2 µmol/ml/hr, n=45, p=0.007), trending higher in subjects with PHT. Arginase activity correlated with the arginine-to-ornithine ratio (r=−0.33, p=0.0004), and lower ratios were associated with greater severity of pulmonary hypertension (1.1±0.4 (controls) vs. 0.8±0.4 (SCD without PHT) vs. 0.6±0.3 (SCD with PHT), controls vs. SCD without pulmonary hypertension vs. SCD with pulmonary hypertension, respectively, p=0.01).

Plasma arginase activity correlated with markers of increased hemolytic rate, including LDH (r=0.44, p<0.001), AST (r=0.39, p<0.002), reticulocyte count (r=0.25, p<0.001), and Hct (r=−0.25, p<0.001), and was higher in erythrocytes of SCD patients compared to controls (37.7±2.9, n=16 vs 23.5±1.7 nmol/mg/min, n=45, p<0.0001), consistent with hemolytic erythrocyte arginase.

These data support a mechanism of disease whereby hemolysis not only liberates vasoactive hemoglobin but also releases erythrocyte arginase, which contributes to impaired nitric oxide bioavailability, endothelial dysfunction, and PHT. The arginine-to-ornithine ratio, a reflection of arginase activity, is a useful biomarker of disease severity, since patients having more severe disease also consistently presented with lower arginine-to-ornithine ratios. Specifically the data above show that the Arg-to-Orn ratio is a biomarker of arginase activity that correlates with the severity of PH in sickle cell disease.

Example 8

Decreased Arginine Bioavailability Contributes to the Pathogenesis of Pulmonary Arterial Hypertension Alterations in amino acid metabolism occurring in pulmonary artery hypertension (PAH) that could be impacted by elevated arginase activity were investigated. Plasma amino acids were determined in normal (NL) controls and patients diagnosed with primary pulmonary hypertension (PH) or PAH associated with scleroderma or systemic lupus erythematosis. These data are provided in the table below.

| Variable | NL Control (n = 36) | PAH (n = 20) | p* |
|---|---|---|---|
| Arginine (µM) | 67 ± 18 | 50 ± 15 | <0.01 |
| Ornithine (µM) | 62 ± 22 | 102 ± 30 | <0.001 |
| Arg/Orn ratio | 1.2 ± 0.5 | 0.6 ± 0.4 | <0.001 |
| Glutamic acid (µM) | 38 ± 15 | 127 ± 75 | <0.001 |
| Proline (µM) | 161 ± 48 | 202 ± 65 | <0.01 |
| Citrulline (µM) | 25 ± 11 | 38 ± 14 | <0.001 |

Plasma Arg levels were low, Orn levels were high, and the Arg-to-Orn ratio was low in PAH as compared to normal controls. Consistent with a shift in Arg metabolism away from NO production and towards the ornithine-dependent pathways, both glutamic acid and proline levels were elevated in PAH. Citrulline levels were also high in PAH. Since Arg is produced from citrulline in the kidneys, renal dysfunction may also contribute to decreased Arg bioavailability. The Arg/[Orn+Citrulline] ratio correlated with mean pulmonary artery pressure measured on cardiac catheterization (r=−0.68, p<0.01), and likely incorporates the impact of arginase activity and decreased Arg bioavailability due to renal impairment.

Decreased Arg bioavailability and a shift of metabolism towards ornithine-dependent pathways are play a role in PAH, again supporting the use of therapies that maximize Arg and NO bioavailability in treatment of such conditions.

Example 9

Decreased Arginine Bioavailability and Elevated Arginase Activity in Thalassemia Data on the levels of amino acids and arginase activity in plasma samples obtained from thalassemia ("thal") patients was collected (8 thal-major, 4 E-beta thal, 2 Hb H alpha thal). All but 3 patients were on chronic transfusion therapy. Echo results were available on 9 patients and demonstrated 6/9 with a tricuspid regurgitant jet velocity ≧2.5 m/s. The data are provided in the table below.

| Variable | NL Control (n = 36) | Thalassemia (n = 14) | p* |
|---|---|---|---|
| Arginine (µM) | 67 ± 18 | 57 ± 26 (50) | 0.15 |
| Ornithine (µM) | 62 ± 22 | 85 ± 68 | 0.05 |
| Arg/Orn ratio | 1.2 ± 0.5 | 0.79 ± 0.4 | <0.01 |
| Proline (µM) | 161 ± 48 | 258 ± 116 | <0.001 |
| Citrulline (µM) | 25 ± 11 | 42 ± 17 | <0.001 |
| Arginase (µmol/cc/hr) | 0.33 ± 0.2 (n = 45) | 0.71 ± 0.3 | <0.001 |

Plasma arginine concentration trended lower in patients with thalassemia, with values ranging from normal to very low (19.5 to 122 µM, median 50 µM). Ornithine levels were high, and the arginine-to-ornithine ratio low in thalassemia patients. Plasma arginase activity was significantly elevated, although a range of values is observed (0.06-1.17 µmol/cc/hr, median 0.83 µmol/cc/hr). Proline was also elevated, a downstream metabolite of arginase activity and likely a contributor to pulmonary vascular remodeling. Of interest, exhaled nitric oxide levels were also significantly elevated in thalassemia (49±41 parts per billion vs. 18±8 ppb, p=0.02 thal vs. normal controls), suggesting an upregulation of nitric oxide synthase in the lungs of patients with thalassemia in addition to higher plasma arginase activity.

These data indicate that the Arg:Orn ratio is an indicator of disease in thalassemia, and further that thalassemia patients are candidates for therapy according to the invention.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method of testing a sample from a human subject having or suspected of having a condition having elevated arginase activity, the method comprising:
   a) detecting a level of arginine and a level of ornithine in a biological sample from the subject, where the biological sample comprises blood, plasma, or serum; and
   b) determining a ratio of the arginine level to the ornithine level,
   wherein an arginine to ornithine ratio of more than 25% reduced versus
      i) a normal arginine:ornithine ratio value, wherein a normal arginine:ornithine ratio is greater than 1.5; or
      ii) a normal control sample arginine:ornithine ratio value,
   indicates that the subject has a condition having elevated arginase activity, and wherein the condition is at least one of acute exacerbation of asthma, sickle cell disease, pulmonary hypertension, pulmonary arterial hypertension (PAH), and thalassemia.

2. The method of claim 1, wherein the subject has or is suspected of having acute exacerbation of asthma.

3. The method of claim 1, wherein the subject has or is suspected of having pulmonary hypertension.

4. The method of claim 3, wherein the pulmonary hypertension is primary pulmonary hypertension, secondary pulmonary hypertension, or persistent pulmonary hypertension of the newborn.

5. The method of claim 1, wherein the subject has or is suspected of having sickle cell disease.

6. The method of claim 1, wherein the subject has or is suspected of having thalassemia.

7. The method of claim 1, wherein the subject has or is suspected of having pulmonary arterial hypertension.

8. The method of claim 1, wherein the PAH is associated with scleroderma.

9. The method of claim 1, wherein the PAH is associated with systemic lupus erythematosus.

10. The method of claim 1, wherein the biological sample is blood.

11. The method of claim 1, wherein the biological sample is plasma.

12. The method of claim 1, wherein the biological sample is serum.

* * * * *

UNITED STATES PATENT AND TRADEMARK OFFICE
CERTIFICATE OF CORRECTION

| | |
|---|---|
| PATENT NO. | : 7,651,846 B2 |
| APPLICATION NO. | : 11/002956 |
| DATED | : January 26, 2010 |
| INVENTOR(S) | : Claudia R. Morris |

Page 1 of 1

It is certified that error appears in the above-identified patent and that said Letters Patent is hereby corrected as shown below:

Please replace the Statement Regarding Government Rights beginning on column 1, line 16, with the following revised statement:

GOVERNMENT RIGHTS

-- This invention was made with government support under federal grant nos. RR0127119 and HL-04386-01 awarded by the National Institutes of Health. The United States Government has certain rights in this invention. --

Signed and Sealed this

Fifteenth Day of June, 2010

David J. Kappos
*Director of the United States Patent and Trademark Office*

UNITED STATES PATENT AND TRADEMARK OFFICE
CERTIFICATE OF CORRECTION

PATENT NO. : 7,651,846 B2  Page 1 of 1
APPLICATION NO. : 11/002956
DATED : January 26, 2010
INVENTOR(S) : Claudia R. Morris It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 90 days.

Signed and Sealed this

Twenty-third Day of November, 2010

David J. Kappos
*Director of the United States Patent and Trademark Office*

UNITED STATES PATENT AND TRADEMARK OFFICE
CERTIFICATE OF CORRECTION

PATENT NO. : 7,651,846 B2
APPLICATION NO. : 11/002956
DATED : January 26, 2010
INVENTOR(S) : Claudia R. Morris It is certified that error appears in the above-identified patent and that said Letters Patent is hereby corrected as shown below:

In the Specification

In Column 1, Lines 17-21, please replace the GOVERNMENT RIGHTS section with the following:
-- This invention was made with government support under grants HL004386 and RR127119 awarded by the National Institutes of Health. The government has certain rights in the invention. --

This certificate supersedes the Certificate of Correction issued June 15, 2010.

Signed and Sealed this
Twelfth Day of November, 2024

Katherine Kelly Vidal
*Director of the United States Patent and Trademark Office*